US012667590B2

(12) United States Patent
Werneth et al.

(10) Patent No.: US 12,667,590 B2
(45) Date of Patent: Jun. 30, 2026

(54) ABLATION EQUIPMENT FOR DELIVERING NON-THERMAL ENERGY TO TREAT TARGET REGIONS OF TISSUE IN ORGANS AND CONTROL METHOD THEREOF

(71) Applicant: Arga' Medtech SA, Chardonne (CH)

(72) Inventors: Randell L. Werneth, San Diego, CA (US); Marshall Sherman, Cardiff by the Sea, CA (US)

(73) Assignee: Argá Medtech SA, Epalinges (CH)

( * ) Notice: Subject to any disclaimer, the term of this patent is extended or adjusted under 35 U.S.C. 154(b) by 792 days.

(21) Appl. No.: 17/939,465

(22) Filed: Sep. 7, 2022

(65) Prior Publication Data

US 2023/0241100 A1    Aug. 3, 2023

Related U.S. Application Data

(63) Continuation-in-part of application No. PCT/IB2021/051853, filed on Mar. 5, 2021, and a
(Continued)

(51) Int. Cl.
| | |
|---|---|
| *A61K 33/06* | (2006.01) |
| *A61B 18/00* | (2006.01) |
| *A61B 18/14* | (2006.01) |

(52) U.S. Cl.
CPC .......... *A61K 33/06* (2013.01); *A61B 18/1492* (2013.01); *A61B 2018/00357* (2013.01);
(Continued)

(58) Field of Classification Search
CPC .... A61K 33/06; A61K 31/19; A61B 18/1492; A61B 2018/00357; A61B 2018/00577;
(Continued)

(56) References Cited

U.S. PATENT DOCUMENTS

| | | | |
|---|---|---|---|
| 5,807,324 A | 9/1998 | Griffin, III | |
| 5,882,346 A | 3/1999 | Pomeranz et al. | |

(Continued)

FOREIGN PATENT DOCUMENTS

| | | | |
|---|---|---|---|
| EP | 2155096 | * | 2/2010 |
| EP | 2664295 | | 11/2013 |

(Continued)

OTHER PUBLICATIONS

WIPO, International Search Report and Written Opinion mailed Jun. 4, 2021, in PCT/IB2021/051853, 15 pgs.
WIPO, International Search Report and Written Opinion mailed Sep. 13, 2021, in PCT/IB2021/051854, 21 pgs.

*Primary Examiner* — Theodore J Stigell
(74) *Attorney, Agent, or Firm* — Bookoff McAndrews, PLLC

(57) ABSTRACT

There is disclosed a composition comprising one or more calcium salts, for use in a treatment or augmenting treatment of non-thermal ablation, the treatment comprising: administering an effective amount of said composition to the subject via a systemic route of administration; delivering non-thermal ablative energy to the target tissue. There is further disclosed ablation equipment for delivering non-thermal energy to treat target regions of tissue in organs, wherein a single power source is configured to generate electric sinusoidal voltage signals to energize each electrode of the equipment; and wherein the single power source is configured to supply at least first and second electrodes that are adjacent to each other on said ablation catheter, with sinusoidal electric voltage signals in phase or out of phase with each other to generate a unipolar electric field and/or a bipolar electric field for delivering the non-thermal energy to the tissue to be treated.

24 Claims, 17 Drawing Sheets

Related U.S. Application Data continuation-in-part of application No. PCT/IB2021/051854, filed on Mar. 5, 2021.

(60) Provisional application No. 62/988,842, filed on Mar. 12, 2020, provisional application No. 62/986,683, filed on Mar. 7, 2020.

(52) U.S. Cl.
CPC ............... *A61B 2018/00577* (2013.01); *A61B 2018/00613* (2013.01); *A61B 2018/0075* (2013.01); *A61B 2018/00767* (2013.01); *A61B 2018/00839* (2013.01)

(58) Field of Classification Search
CPC .. A61B 2018/00613; A61B 2018/0075; A61B 2018/00767; A61B 2018/00839; A61B 2018/00642; A61B 2018/1253; A61B 2018/1467; A61B 18/1206; A61B 18/14; A61B 2018/00351; A61B 2018/1226; A61B 2018/124; A61B 2018/126; A61P 9/00; A61P 9/06
See application file for complete search history.

(56)     References Cited

U.S. PATENT DOCUMENTS

| | | | |
|---|---|---|---|
| 9,943,599 B2 | 4/2018 | Gehl et al. | |
| 2002/0077627 A1* | 6/2002 | Johnson | A61B 18/18 606/41 |
| 2012/0101494 A1 | 4/2012 | Cadouri et al. | |
| 2014/0066913 A1* | 3/2014 | Sherman | A61B 18/1492 606/41 |
| 2016/0051324 A1* | 2/2016 | Stewart | A61N 1/327 606/41 |
| 2017/0035499 A1 | 2/2017 | Stewart et al. | |
| 2019/0125788 A1* | 5/2019 | Gruba | A61K 9/0009 |
| 2019/0350647 A1* | 11/2019 | Ramberg | A61N 1/327 |
| 2021/0052882 A1 | 2/2021 | Wasson et al. | |

FOREIGN PATENT DOCUMENTS

| | | | |
|---|---|---|---|
| WO | 2017192804 | | 11/2017 |
| WO | 2019133608 | | 7/2019 |
| WO | WO-2021044312 | * | 3/2021 |

* cited by examiner

ABLATION EQUIPMENT FOR DELIVERING NON-THERMAL ENERGY TO TREAT TARGET REGIONS OF TISSUE IN ORGANS AND CONTROL METHOD THEREOF

RELATED APPLICATIONS

This application is a continuation-in-part of International Patent Application No. PCT/IB2021/051853, filed on Mar. 5, 2021. International Patent Application No. PCT/IB2021/051853 claims priority to U.S. Provisional Patent Application No. 62/986,683, filed on Mar. 7, 2020, and U.S. Provisional Patent Application No. 62/988,842, filed on Mar. 12, 2020. International Patent Application No. PCT/IB2021/051853, U.S. Provisional Patent Application No. 62/986,683, and U.S. Provisional Patent Application No. 62/988,842 are each incorporated herein by reference.

This application is a continuation-in-part of International Patent Application No. PCT/IB2021/051854, filed on Mar. 5, 2021. International Patent Application No. PCT/IB2021/051854 claims priority to U.S. Provisional Patent Application No. 62/986,683, filed on Mar. 7, 2020. International Patent Application No. PCT/IB2021/051854 and U.S. Provisional Patent Application No. 62/986,683 are each incorporated herein by reference.

FIELD OF THE INVENTION

The present invention relates to a method for performing non-thermal ablation of a target tissue in an organ or tissue of a patient. In particular, the present invention relates to a method for performing non-thermal ablation of a target tissue which comprises delivering non-thermal ablative energy to the target tissue to be ablated, particularly Irreversible Electroporation (IRE).

More particularly, the present invention relates to a method for mostly non-thermally ablating target tissue. Said tissue would be that which is either diseased such as in atrial fibrillation (or AF) patient where the cardiac cell action potential is not normal, having a slow or rapid action potential. Said tissue could be scar tissue, tissue with low-voltage signals, tissue that is deemed necessary to ablate in order to block a refractory wave-front, tissue causing an arrhythmia, and/or any tissue necessary to stop or prevent irregular arrhythmias in patients.

The present invention provides a combination treatment system that has at least one energy delivery device, or ablation catheter, and at least one energy or power source, or single power source, that is capable of providing non-thermal energy, particularly Irreversible Electroporation (IRE) energy, to the energy delivery device.

The present invention further relates to: a method for controlling at least a plurality of electrodes; an ablation catheter kit; a method for the treatment of various conditions; the use of a kit to treat both the left and right atria of a heart.

Yet further, the present invention relates to: a composition comprising one or more calcium salts; a method for performing non-thermal ablation, or for augmenting non-thermal ablation, of target tissue in an organ; use of a composition comprising one or more calcium salts; and a kit.

BACKGROUND

Tissue ablation is used in numerous medical procedures to treat a patient. Tissue ablation can be performed to kill (remove from the normal hearts conduction system) undesired tissue such as diseased cardiac cells. Cardiac ablation procedures may also involve the modification of the tissues substrate in order to change or stop electrical function in a particular area in the chain of electrical propagation through the heart tissue in patients with an arrhythmia condition. In tumors, ablation is performed to kill the tumor and prevent its spread to normal healthy tissue.

The ablation can be performed by passing energy, such as electrical energy, through one or more electrodes and causing tissue modification and/or death where the electrodes are in contact. Ablation procedures can be performed on patients with any cardiac arrhythmia such as atrial fibrillation (or AF), ventricular tachycardia (or VT) by ablating tissue in the heart.

Mammalian organ function typically occurs when electrical activity is spontaneously generated by the SA node, the cardiac pacemaker. This electrical impulse is propagated throughout the right atrium, and through Bachmann's bundle to the left atrium, stimulating the myocardium of the atria to contract. The conduction system consists of specialized heart muscle cells. Cardiac myocardial cell has a negative membrane potential when at rest. Stimulation above a threshold value induces the opening of voltage-gated ion channels and a flood of cations into the cell. The positively charged ions entering the cell cause the depolarization characteristic of an action potential. Like skeletal muscle, depolarization causes the opening of voltage-gated calcium channels and release of $Ca2+$ from the t-tubules. This influx of calcium causes calcium-induced calcium release from the sarcoplasmic reticulum, and free $Ca2+$ causes muscle contraction. After a delay, potassium channels reopen, and the resulting flow of $K+$ out of the cell causes repolarization to the resting state. This transmission of electrical impulses propagates through the heart chamber. A disturbance of such electrical transmission may lead to organ malfunction. One particular area where electrical impulse transmission is critical for proper organ function is in the heart, resulting in atrial contractions which leads to the pumping of blood into the ventricles in a manner synchronous with the pulse.

Atrial fibrillation (AF) refers to a type of cardiac arrhythmia where there is disorganized electrical conduction in the atria causing rapid uncoordinated atrial contractions that result in ineffective pumping of blood into the ventricle as well as a lack of synchrony. During AF, the atrioventricular node receives electrical impulses from numerous locations throughout the atria instead of only from the sinus node. These aberrant signals overwhelm the atrioventricular node, producing an irregular and rapid heartbeat. As a result, blood may pool in the atria, increasing the likelihood of blood clot formation. The major risk factors for AF include age, coronary artery disease, rheumatic heart disease, hypertension, diabetes, and thyrotoxicosis. AF affects 7% of the population over age 65.

Atrial fibrillation treatment options are limited.

Lifestyle changes only assist individuals with lifestyle related AF. Medication therapy manages AF symptoms, often presents side effects more dangerous than AF, and fails to cure AF. Electrical cardioversion attempts to restore a normal sinus rhythm, but has a high AF recurrence rate due to disease progression. In addition, if there is a blood clot in the atria, cardioversion may cause the clot to leave the heart and travel to the brain (causing a stroke) or to some other part of the body. What are needed are new methods for treating AF and other medical conditions involving disorganized electrical conduction.

Various ablation techniques have been proposed to treat AF, including the Cox-Maze ablation procedure, linear ablation of various regions of the atrium, and circumferential ablation of pulmonary vein ostia. The Cox-Maze ablation procedure and linear ablation procedures are tedious and time-consuming, taking several hours to accomplish. Current pulmonary vein ostial ablation is proving to be effective in the short-term but ineffective long-term. All ablation procedures involve the risk of inadvertently damaging untargeted tissue, such as the esophagus while ablating tissue in the left atrium of the heart. There is therefore a need for improved atrial ablation products and techniques that create efficacious lesions in a safe manner.

Cardiology applications which could be non-thermal or nearly non-thermal ablation are vast and include treating patients with atrial fibrillation, ventricular fibrillation, septal ablation, and vascular structures diseases. The application of ablation would be more appealing if its characteristics included the ability to be tissue specific.

Cardiac ablation technology for medical treatment is known in the art and includes such treatment modalities as radiofrequency (RF), focused ultrasound, such as high intensity ultrasound beams, microwave, laser, thermal electric heating, traditional heating methods with electrodes using Direct Current (DC) or Alternating Current (AC), and application of heated fluids and cold therapies (such as cryosurgery, also known as cryotherapy or cryoablation).

In many of these procedures an energy delivery device, such as a probe with or without a needle, is inserted into a target tissue to cause destruction of a target region of the cardiac tissue through the application of energy, such as thermal energy, non-thermal energy, and energy associated with cryo ablation procedures.

In procedures where it is necessary to deliver this energy inside the heart or organ, the insertion of the energy delivery device into the heart chamber or other organs is accomplished by an elongated catheter which is typically created from points inferior to the heart. The ablation catheter comprises an elongated shaft with a proximal portion including a proximal end and a distal end, and a distal portion with a proximal end and a distal end. The elongated shaft further comprises a shaft ablation assembly and a distal ablation assembly configured to deliver energy, such as RF and/or IRreversible Electroporation (IRE) energy, to tissue. The shaft ablation assembly is proximal to the distal end of the distal portion, and includes at least one shaft ablation element or electrode fixedly or removably attached to the shaft and configured to deliver ablation energy to tissue. The distal ablation assembly is at the distal end of the distal portion and includes at least one tip ablation element configured to deliver ablation energy to tissue.

Cardiac arrhythmias, such as ventricular tachycardia (VT) and atrial fibrillation (AF), have significant morbidity and mortality, including stroke, heart failure, and sudden death. Medical therapy alone is often not successful, and radiofrequency (RF) catheter ablation has become the standard of care for the treatment of all drug refractory arrhythmias. Efficacy of catheter ablation for the treatment of arrhythmias is dependent on the ability of RF to create durable lesions. Inability to render the arrhythmogenic tissue electrically inert can lead to arrhythmia recurrences. Furthermore, ablation safety is dependent on a high level of precision to avoid unintended injury to adjacent tissue. Achieving lesion durability while maintaining ablation precision remains a challenge with current technology.

Irreversible Electroporation (IRE) ablation is a new and nearly non-thermal approach for increasing tissue ablation efficacy. The cellular effects depend on the applied electric field, which is determined by pulse duration, voltage, frequency, and polarity. Higher strength electric fields cause significant changes in cell membrane permeability, which leads to a cell apoptotic process, with depletion of ATP and increased intracellular calcium concentrate, resulting in cell death. However, applying higher strength electric fields across the tissue is associated with complication or adverse effect to the tissue.

The interaction of the cell membrane with high intensity pulsed electric fields is widely used to provoke the transient permeabilization of the cell membrane in electroporation, also known as electropermeabilization. This is routinely used as a technique to incorporate membrane-impermeant molecules into the cell.

Using ultra short but strong electrical fields creates permanent and hence lethal nanopores in the cell membrane, to disrupt cellular homeostasis. The resulting cell death results from apoptosis and not necrosis as in all other thermal or radiation-based ablation techniques.

Typically, this is performed with a Direct Current (DC) or a Square-wave pulse, which cause significant cardiac muscle stimulation. Therefore, they are not ideal for ensuring the overall safety of the subject having the ablation procedure.

In particular, square wave electric signals distribute the energy applied to cells in a wide frequency band. However, using the square wave high intensity pulsed electric field causes strong muscle contraction due to direct stimulation of the neuromuscular junction, which requires special anesthesia and total body paralysis of the patient.

Examples of square wave voltage signals SW1, SW2 that are currently used to deliver Irreversible Electroporation (IRE) energy to ablate cardiac tissue are shown in FIGS. 6A, 6B. Particularly, a monophasic square wave voltage signal SW1 of FIG. 6A causes the current to travel in one-direction, from the electrode to the tissue to be treated, therefore all energy is above a reference value, similar to Direct Current. This causes cardiac muscle stimulation and requires the need for general anesthesia of the patient. A biphasic square wave voltage signal SW2 of FIG. 6B causes the current to travel between two adjacent electrodes, resulting in minimal stimulation and requires only sedation. Since both monophasic and biphasic square wave voltage signals cause significant cardiac muscle stimulation, they are not ideal for ensuring the overall safety of the subject having the ablation procedure.

Therefore, need is felt for an efficient solution for the non-thermal ablation of a target tissue of a patient which is safer for the patient. More in particular, need is felt for a solution for augmenting the non-thermal ablation of a target tissue without increasing the electric field strength across the tissue, which is associated with complications or adverse effects to the tissue. The use of an alternative solution for delivering non-thermal, irreversible electroporation energy would be highly desirable and safer for patients.

SUMMARY

It is a purpose of this invention, in certain embodiments, to provide a method for augmenting ablation of a target tissue in a subject in need thereof, which comprises: (a) administering to a subject in need thereof an effective amount of one or more similar and/or dissimilar agents ("agent" herein), where this administration increases the apoptotic effect of electroporation (e.g. without increasing electric field strength); and (b) applying an electric field energy to the target tissue in the subject, wherein the agent increases the apoptotic effect and/or reparative cellular process induced in the target tissue by application of the electric field energy to the target tissue, such as to minimize the need for stronger electric fields across the tissue and the potential heat damage/risk effects. In certain embodiments, the agent that increases the apoptotic effect of electroporation without increasing electric field strength comprises a highly conductive medium. In some embodiments, agent delivery is configured to increase conductivity of the medium to a level of at least 0.5 S/m, or at least 0.7 S/m. In some embodiments, calcium and/or another agent as described herein is delivered locally, such as directly into and/or otherwise the cardiac tissue being treated. In certain embodiments, the agent increases the conductivity when present in the extracellular medium, increasing cell permeability, and correspondingly lowering cell death threshold.

It is a purpose of this invention, in certain embodiments, to provide a method for augmenting ablation of a target tissue in a subject in need thereof, which comprises: administering to the subject an effective amount of an agent that causes significant changes in cell membrane permeability, which leads to a cell apoptotic process, with depletion of ATP and increased intracellular calcium concentrate, by application of ablative energy to the target cardiac tissue. For example, said agent is a calcium agent and/or a calcium compound. The terms "calcium agent" and "calcium compound" are intended to denote an agent or compound which is able to release calcium ions, for example calcium salts. In some embodiments, the agent comprises multiple agents (e.g. multiple similar and/or dissimilar agents).

It is a purpose of this invention, in certain embodiments, to provide a method for treating a cardiac arrhythmia in a subject in need thereof, which comprises: (a) performing a method for augmenting ablation of a target cardiac tissue in the subject; and (b) applying an electric field energy to the target cardiac tissue in the subject, thereby treating the subject in need of augmented ablation of the target cardiac tissue.

It is a purpose of this invention, in certain embodiments, to provide a method for augmenting electroporation ablation of a target tissue in a subject in need thereof, the method comprising: (a) administering to a subject in need thereof an effective amount of an agent that modulates apoptotic effects and/or decreases ATP in a target tissue by application of an ablative electroporation energy to the target tissue; and (b) applying an ablative electroporation energy to the target tissue to be ablated in the subject, wherein the agent modulates the protective and/or reparative cellular process, thereby sensitizing the target tissue to the ablative energy, and augmenting electroporation ablation of the target tissue in the subject. In some embodiments, the delivery of the calcium and/or another agent to the patient is performed within 60 minutes, or within 30 minutes of the delivery of the electroporation energy.

As used herein, "modulate" or "modulating" refer to changing the rate at which a particular process occurs, thereby decreasing or increasing a particular effect, thereby inhibiting a particular process, reversing a particular effect or process, and/or preventing the initiation of a particular effect or process.

In an aspect, the presently disclosed subject matter contemplates any agent that modulates apoptotic effects and/or ATP in a target tissue by application of an ablative electroporation energy to the target tissue. Exemplary agents include, without limitation, calcium and/or calcium compounds that will change, increase or decrease conductivity of intercellular medium. In some embodiments, agent delivery is configured to increase conductivity of the medium to a level of at least 0.5 S/m, or at least 0.7 S/m.

As used herein, the term "change conductivity of intercellular medium" can refer to an effect provided by agents that are "natural product-like". However, the term "change conductivity of intercellular medium" is not limited to effects of "natural product-like" agents.

It is a purpose of this invention, in certain embodiments, to provide a method that modulates any cellular and/or reparative process induced by ablative electroporation energy in a target tissue, thereby changing the apoptotic sensitization of the target tissue to the ablative electroporation energy, and augmenting the electroporation ablation of the target tissue.

It is a purpose of this invention, in certain embodiments, to provide a method for augmenting electroporation ablation of a target tissue in a subject in need thereof, which comprises: (a) administering to a subject in need thereof an effective amount of at least one agent that modulates inflammation and/or a pro-fibrotic reaction in a target tissue to be electroporation ablated in the subject; and (b) applying an electroporation ablative energy to the target tissue to be ablated in the subject, wherein the at least one agent modulates inflammation and/or the pro-fibrotic reaction in the target tissue to be electroporation ablated in the subject, thereby increasing the sensitization of the target tissue to the ablative energy, and augmenting ablation of the target tissue in the subject. In some embodiments, multiple similar and/or dissimilar agents are administered.

In certain embodiments, the agent modulates (e.g. the administration of the agent modulates) inflammation in a target cardiac tissue to be electroporation ablated, thereby increasing the sensitization of the target cardiac tissue to the electroporation energy, and augmenting electroporation of the target cardiac tissue.

In certain embodiments, the agent modulates a pro-fibrotic reaction in a target tissue, for example cardiac tissue, to be exposed to electroporation, thereby increasing the sensitization of the target tissue to the electroporation energy, and augmenting electroporation of the target cardiac tissue.

In certain embodiments, the agent modulates inflammation and a pro-fibrotic reaction in a target cardiac tissue to be ablated, thereby increasing the sensitization of the target cardiac tissue to the ablative energy, and augmenting ablation of the target cardiac tissue.

Examples of ablative electroporation energy that can be augmented by modulating inflammation and/or the pro-fibrotic reaction in a target tissue include, without limitation, non-thermally ablative energy, such as high voltage, short duration electrical energy.

Those skilled in the art will appreciate that the cellular response to non-thermal tissue injury within the electroporation ablation periphery is complex and multifaceted. It is believed that cellular stressors lead to up-regulation of oxidative pathways that induce apoptosis, and counterbalancing such stressors are reparative pathways that have cellular protective effects against apoptosis, especially the production of heat shock proteins in response to non-thermal injury.

The ablative electroporation energy is a non-thermal energy.

As used herein, the terms "decrease," "reduce," or "inhibit," and grammatical derivations thereof, refer to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

It is a purpose of this invention, in certain embodiments, to provide a method for augmenting electroporation ablation of a target cardiac tissue in a subject in need thereof, which comprises administering to a subject in need thereof an effective amount of an agent (e.g. one or more similar and/or dissimilar agents), where this administration increases the apoptotic effect when an electric field is applied across the targeted tissue.

In certain embodiments, the method includes administering to the subject a composition comprising an effective amount of a toxin (e.g., a myocardial toxin), for example, by targeting the toxin to a target tissue to be ablated via non-thermal approaches, for example, using a presently disclosed composition comprising electroporation. In some embodiments, the toxin is provided in a carrier substance that is configured to release the toxin when exposed to an electric field. In some embodiments, the present invention includes the administration of a toxin-based agent and a calcium-based agent in combination, where the two agents synergistically or otherwise improve an electroporation delivery (e.g. decrease the level of electric field delivered and/or improve one or more desired effects of the electroporation).

In certain embodiments, the present invention provides a method for non-thermal ablation, or for augmenting non-thermal ablation, of a target tissue of a patient, which comprises administering a calcium agent or a calcium compound, to the patient, and delivering non-thermal ablative energy to the target tissue to be ablated.

In a first aspect, the present invention relates to a composition comprising one or more calcium salts, for use in a treatment of non-thermal ablation, or for use in augmenting a treatment of non-thermal ablation, of a target tissue in an organ of a subject in need thereof, wherein the treatment comprises:
    a) administering an effective amount of a composition comprising one or more calcium salts to the patient via a systemic route of administration; and
    b) delivering non-thermal ablative energy to the target tissue to be ablated, wherein said step a) is carried out before, during, and/or after said step b). In some embodiments, the delivery of the calcium and/or another agent to the patient is performed within 60 minutes, or within 30 minutes of the delivery of the electroporation energy.

In a second aspect, the present invention relates to a method for performing non-thermal ablation, or augmenting non-thermal ablation, of a target tissue in an organ of a patient, wherein the method comprises:
    a) administering an effective amount of said composition comprising one or more calcium salts to the subject via a systemic route of administration; and
    b) delivering non-thermal ablative energy to the target tissue to be ablated, wherein said step a) is carried out before, during, and/or after said step b). In some embodiments, the delivery of the calcium and/or another agent to the patient is performed within 60 minutes, or within 30 minutes of the delivery of the electroporation energy.

In a third aspect of the invention, the present invention relates to the use of a composition comprising one or more calcium salts, for the manufacture of a medicament for a treatment of non-thermal ablation, or for augmenting a treatment of non-thermal ablation, of a target tissue in an organ of a subject in need thereof, the treatment comprising:
    a) administering an effective amount of said composition to the subject via a systemic route of administration;
    b) delivering non-thermal ablative energy to the target tissue to be ablated, wherein said step a) is carried out before, during, and/or after said step b). In some embodiments, the delivery of the calcium and/or another agent to the patient is performed within 60 minutes, or within 30 minutes of the delivery of the electroporation energy.

According to a preferred embodiment of the invention, said step a) is carried out at least before said step b). According to a particular embodiment of the invention, said step a) is carried out only before said step b).

In a fourth aspect, the present invention relates to a kit comprising:
    a composition comprising one or more calcium salts, and
    an ablation equipment for delivering non-thermal energy, the ablation equipment comprising an ablation catheter and a single power source;
    said ablation catheter comprising:
    a catheter elongated shaft comprising at least an elongated shaft distal portion;
    said catheter elongated shaft comprising a flexible body to navigate through body vessels;
    said ablation catheter further comprising a shaft ablation assembly disposed at said elongated shaft distal portion;
    said shaft ablation assembly comprising at least a plurality of electrodes fixedly disposed at said elongated shaft distal portion;
    all electrodes of said at least a plurality being electrically connected to the single power source,
    said single power source being configured to generate sinusoidal electric voltage signals to energize each electrode for delivering the non-thermal energy.

In another aspect, the present invention relates to a kit as defined above for use in a treatment of non-thermal ablation, or for use in augmenting a treatment of non-thermal ablation, of a target tissue in an organ of a subject in need thereof.

The terms "subject" and "patient" are used interchangeably herein. The subject treated by the method according to the present invention is desirably a human subject, although it is to be understood that the methods described herein are effective with respect to all vertebrate species, which are intended to be included in the term "subject."

The expression "for use in augmenting a treatment of non-thermal ablation" is intended to denote "for augmenting the effect of non-thermal ablation treatment", "for increasing the effectiveness of non-thermal ablation treatment", "for reducing one or more risks associated with non-thermal ablation treatment", and/or "for simplifying a non-thermal ablation treatment".

The expression "for use in augmenting a treatment of non-thermal ablation" is also referred to as "for use in augmenting non-thermal ablation" or "for use in augmenting electroporation ablation".

As used herein, the expression "augmenting electroporation ablation" broadly refers to increasing ablation lesion size (e.g., average maximum depth, maximum diameter, maximum surface diameter, volume, etc.), a greater reduction in electrical conductivity, and/or increased electric field effect (e.g., increased apoptotic effect from an electric field in target tissue adjacent to an ablation catheter tip) in a target tissue ablated using the composition and method according to the invention, compared to ablation lesion size and electrical conductivity in a target tissue ablated without using the composition and method according to the invention. Advantageously, the composition and method according to the invention create larger lesions without increasing the incidence of heat and without increasing the electrical field.

As used in some contexts herein, the expression "augmenting electroporation ablation" refers to increasing sensitization of a target tissue to apoptotic effects from an electrical field ablative energy, for example, by modulating ATP levels in the cells.

As used herein, the expression "augmenting electroporation ablation" may also refer to at least one of the following: improving lesion durability; enhancing ablation efficiency; enhancing ablation lesions using lower power energy; enhancing ablation lesions without requiring higher power ablative energy that is associated with complications or adverse effects to target tissue or surrounding tissue or increase in temperatures of tissue; decreasing heterogeneity at the periphery of targeted tissue and myocardial infarct scar after electroporation energy, thereby decreasing post-ablation arrhythmia susceptibility.

The expression "target tissue to be ablated" is intended to denote at least a region (e.g. at least a volume) of the target tissue to be ablated.

The expressions "target tissue to be ablated" and "target tissue to be treated" are used indifferently in the description below.

Advantageously, said composition comprising one or more calcium salts is a calcium-ion-containing composition. The composition comprising one or more calcium salts may also be referred to herein below as "calcium-ion-containing composition". The one or more calcium salts contained in said composition may also be referred to herein below, more generally, as a calcium agent or calcium compound.

Advantageously, administering calcium ions (Ca2+) promotes additional cell death associated with delivering non-thermal ablative energy to the target tissue to be ablated. Delivering non-thermal energy to the target tissue to be ablated causes the formation of pores in the cells and then cell death, causing apoptosis of the cells receiving the non-thermal energy.

Advantageously, non-thermal ablative energy induces permeabilization of cells membrane, which results in an increased uptake of calcium leading to increased intracellular calcium concentration and ATP depletion associated with cell death.

Advantageously, electroporation plus calcium ions increases the apoptotic effect and decreases the body's protective and/or reparative cellular processes.

Advantageously, calcium ions modulate apoptotic effects and/or ATP levels in a target tissue by application of an ablative electroporation energy to the target tissue.

Advantageously, calcium ions increase the apoptotic effect when an electric field is applied across the targeted tissue or other means. Advantageously, this results in a decrease of ATP levels.

Advantageously, calcium ions modulate a protective and/or reparative cellular process induced in a target tissue by application of electroporation to the target tissue.

Advantageously, calcium ions increase the cardiac muscle cells apoptotic effect when an electric field is applied across the targeted tissue.

Without being bound by theory, it is believed that calcium causes significant changes in cell membrane permeability, which leads to a cell apoptotic process, with depletion of ATP and increased intracellular calcium concentrate in the target tissue, by application of electroporation ablative energy to the target tissue. This results in cell death by application of the electroporation to the target tissue, thereby sensitizing the target tissue to the electroporation energy, and augmenting electroporation ablation of the target tissue in the subject. In some embodiments, the significant changes in cell membrane permeability, which leads to a cell apoptotic process, with depletion of ATP and increased intracellular calcium concentrate, modifies the target tissue to be ablated.

According to an embodiment of the invention, said one or more calcium salts are soluble.

According to an embodiment of the invention, said one or more calcium salts are selected among calcium halide salts, calcium salts of organic acids, calcium phosphate, and combinations thereof.

According to an embodiment of the invention, said one or more calcium salts are selected from group the consisting of: calcium chloride, calcium bromide, calcium iodide, calcium lactate, calcium citrate, calcium malate, calcium acetate, calcium gluconate, calcium propionate, calcium ascorbate, calcium butyrate, calcium formate, calcium citrate malate, calcium lactate malate, calcium lactate gluconate, calcium lactate citrate, calcium phosphate, and combinations thereof. In some embodiments, at least two, or at least three of the calcium salts are administered to the patient (e.g. prior to, during, and/or after non-thermal energy delivery).

According to an embodiment of the invention, at least one of said one or more calcium salts is calcium gluconate.

According to an embodiment of the invention, said composition comprising one or more calcium salts is a calcium-ion-containing solution. According to this embodiment, the composition comprises said one or more calcium salts and a liquid carrier. Preferably, said liquid carrier is a physiological acceptable carrier, for example water of a buffer system. According to different embodiments, said liquid carrier is selected among sterile water, physiological saline, phosphate buffer, and/or a solution containing an imaging contrast agent.

According to different embodiments of the invention, the composition comprising said one or more salts, which is contained in the above defined kit, is stored, for example, in a syringe, vial, ampoule, bag, or other container. In a particular embodiment, said composition may be stored as a dry composition, for example, in a syringe, vial, ampoule, bag or other container, and may be mixed with a suitable liquid carrier prior to administration. In an aspect, the kit can be packaged in a divided or undivided container, such as a carton, bottle, ampule, tube, etc. According to different embodiments, the composition can be packaged in dried, lyophilized, or liquid form. Additional components provided can include vehicles for reconstitution of dried components. Preferably all such vehicles are sterile and apyrogenic so that they are suitable for injection into a patient without causing adverse reactions.

In an aspect, the presently disclosed kit contains some or all of the components, reagents, supplies, and the like to practice a method according to the invention. In some embodiments, the term "kit" refers to any intended article of manufacture (e.g., a package or a container) comprising said composition or the components of said composition.

In some embodiments, the kit comprises said composition or the components of said composition, and a set of particular instructions for augmenting ablation of a target tissue in a subject in need thereof, and/or for treating a disease or disorder in a patient (e.g., a cardiac arrhythmia).

According to an embodiment of the invention, said composition can be encapsulated within liposomes. According to this embodiment, said composition is preferably administered to the vascular system of the patient, and liposomes are advantageously used to place the calcium-ion-containing composition into the vascular system of the patient.

According to an embodiment of the invention, said composition further comprises liposomes, and said one or more calcium salts are encapsulated within said liposomes. According to this embodiment, said composition is preferably administered to the vascular system of the patient, and liposomes are advantageously used to place the one or more calcium salts into the vascular system of the patient.

According to an embodiment of the invention, said liposomes are electric field-sensitive liposomes. According to an embodiment of the invention, said liposomes are pulsed electric field-sensitive liposomes.

Advantageously, the liposomes are lysed upon exposure to a threshold electric field, and calcium ions are delivered to the cells where non-thermal ablation is desirable. According to an embodiment, said threshold electric field is from about 0.3 V/nm to about 0.6 V/nm; for example, the electric field-sensitive liposomes can release their contents at an electric field of at least 0.5 V/nm.

According to an embodiment, liposomes are lysed when in contact with electroporation energy, delivering the calcium ions to the cells where electroporation ablation is desirable.

According to an embodiment of the invention, said composition further comprises metallic nanoparticles. In some embodiments, said metallic nanoparticles are encapsulated in the above defined liposomes. In some embodiments, said metallic nanoparticles are encapsulated in electrical-field-sensitive liposomes. In some embodiments, said metallic nanoparticles are encapsulated in liposomes with calcium.

In some embodiments, metallic nanoparticles are added to the calcium/liposome composition to attract the electroporation energy in order to speed up liposome lysing process. In some embodiments, the metallic nanoparticles are used as a wireless electrical antenna. In some embodiments, the electrical-field-sensitive liposomes contain the metallic nanoparticles which attract the electric field similar to a wireless antenna, upon exposure to a threshold electric field. Nanoparticles, such as nanoparticles included with an agent of the present inventive concepts, (e.g. an agent including calcium) can be delivered to one or more location within and/or otherwise proximate the tissue to be treated (e.g. tissue to be non-thermally ablated using electroporation energy).

According to an embodiment, the method according to the invention comprises imaging said metallic nanoparticles in the subject to identify locations where they were released, such as to assess and/or determine where lesion ablation has occurred.

According to an embodiment, the presently disclosed subject matter contemplates imaging target tissue to be ablated. In some embodiments, the presently disclosed methods include imaging the metallic nanoparticles in the subject. In some embodiments, the nanoparticles will create a visual representation of exactly what tissue was ablated under XRay.

In certain embodiments, the metallic nanoparticles are selected from a variety of differently shaped metallic nanoparticles, for example coral-shaped, cube-shaped, rod-shaped, spherical-shaped, tetrapod-shaped, triangular-shaped, and combinations thereof.

Exemplary metallic nanoparticles of use herein include, without limitation, copper nanoparticles, gadolinium nanoparticles, gold nanoparticles, iron nanoparticles, titanium nanoparticles, and combinations thereof. In some embodiments, the nanoparticles can be coated. For example, the metallic nanoparticles (e.g., iron) can be coated with carbon, for example, to impart different paramagnetic properties.

As used herein, the term "nanoparticle" refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 $\mu$m). In such embodiments, the particle also can be referred to as a "microparticle." Thus, the term "microparticle" includes particles having at least one dimension in the range of about one micrometer ($\mu$m), i.e., $1 \times 10-6$ meters, to about 1000 $\mu$m. The term "particle" as used herein is meant to include nanoparticles and microparticles.

According to various embodiments of the invention, said composition comprising one or more calcium salts also comprises an effective amount of at least one Apoptosis Inducers, and/or an effective amount of at least one anticoagulant, and/or an effective amount of at least one anti-inflammatory agent, and/or an effective amount of at least one anti-fibrotic agent, and/or an effective amount of at least one DMSO/Dimethyl sulfoxide agent.

In some embodiments, the composition comprises at least one prophylactic agent. In some embodiments, the composition comprises an antianaphylactic agent. In some embodiments, the composition comprises dexamethasone. In some embodiments, the composition comprises an antihypotensive agent. In some embodiments, the composition comprises epinephrine.

In some embodiments, the composition comprises at least one antiarrhythmic agent. Exemplary antiarrhythmic agents of use herein include, without limitation, amiodarone, bepridil hydrochloride, disopyramide, dofetilide, dronedarone, flecainide, ibutilidie, lidocaine, procainamide, propafenone, propranolol, quinidine, sotalol, tocainide, and combinations thereof.

In some embodiments, the composition comprises at least one calcium channel blocker. Exemplary calcium channel blockers of use herein include, without limitation, amlodipine, diltiazem, felodipine, isradipine, nicardipine, nifedipine, nimodipine, nisoldipine, verapamil, and combinations thereof.

In some embodiments, the composition comprises at least one beta-blocker. Exemplary beta-blockers of use herein include, without limitation, acebutolol, atenolol, betaxolol, bisoprolol/hydrochlorothiazide, carteolol, esmolol, metoprolol, nadolol, penbutolol, pindolol, propranolol, timolol, and combinations thereof.

In some embodiments, the composition comprises at least one anticoagulant. Exemplary anticoagulants of use herein include, without limitation, warfarin and aspirin.

In some embodiments, the composition comprises at least one agent that induces apoptosis. In some embodiments, the composition comprises sonosensitizers. In some embodiments, the composition comprises polynucleotides (e.g., anti-sense, ribozymes, siRNA). In some embodiments, the composition comprises polypeptides (e.g., enzymes and antibodies). In some embodiments, the composition comprises agents that bind (e.g., oligomerize or complex) with a Bcl-2 family protein such as Bax. In some embodiments, the composition comprises alkaloids. In some embodiments, the composition comprises alkylating agents. In some embodiments, the composition comprises antibiotics. In some embodiments, the composition comprises antimetabolites. In some embodiments, the composition comprises hormones. In some embodiments, the composition comprises platinum compounds. In some embodiments, the composition comprises monoclonal or polyclonal antibodies (e.g., antibodies conjugated with anticancer drugs, toxins, defensins). In some embodiments, the composition comprises toxins (e.g., cardiac specific toxins, e.g., myocardial toxins, such as ethanol, botulinum toxin, and tetrodotoxin (TTX)). In some embodiments, the composition comprises radionuclides. In some embodiments, the composition comprises biological response modifiers (e.g., interferons (e.g., IFN-a) and interleukins (e.g., IL-2)). In some embodiments, the composition comprises adoptive immunotherapy agents. In some embodiments, the composition comprises hematopoietic growth factors. In some embodiments, the composition comprises agents that induce cell differentiation (e.g., all-trans-retinoic acid). In some embodiments, the composition comprises gene therapy reagents (e.g., anti-sense therapy reagents and nucleotides). In some embodiments, the composition comprises angiogenesis inhibitors. In some embodiments, the composition comprises proteosome inhibitors. In some embodiments, the composition comprises NF-KB modulators. In some embodiments, the composition comprises anti-CDK compounds. In some embodiments, the composition comprises HDAC inhibitors. In some embodiments, the composition comprises heavy metals (e.g., barium, gold, or platinum). In some embodiments, the composition comprises chemotherapeutic agents (e.g., doxorubicin or cisplatin) and the like. Numerous other examples of toxic compounds are known to those skilled in the art.

In some embodiments, toxic agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); anti-sense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORA-DEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-1 1, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like. Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) *vinca* alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,ρ'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide); and 17) gonadotropin-releasing hormone analogs (e.g., leuprolide).

In some embodiments, the composition comprises an agent that decreases the expression level and/or activity of hsp60. In some embodiments, the composition comprises an agent that decreases the expression level and/or activity of hsp70. In some embodiments, the composition comprises an agent that decreases the expression level and/or activity of hsp90. In some embodiments, the composition comprises quercetin.

In some embodiments, the composition comprises an agent that inhibits procaspase 9 activation. In some embodiments, the composition comprises an agent that prevents cytochrome c release from mitochondria. In some embodiments, the composition comprises an agent that modulates JNK phosphorylation.

As mentioned above, said calcium-ion-containing composition is advantageously administered to the patient via a systemic route of administration. Advantageously, the calcium-ion-containing composition is then delivered to the target tissue to be ablated. Advantageously, the calcium-ion-containing composition reaches the target tissue to be ablated.

The expression "systemic route of administration", also referred to as "systemic administration", "administered systemically", "peripheral administration" and "administered peripherally", as used herein is intended to denote that the composition is administered such that it enters the patient's system and, thus, is subject to metabolism and other like processes, for example, subcutaneous or intravenous administration.

According to different embodiments of the invention, the calcium-ion-containing composition is administered to the patient via a suitable route of administration selected from: intravenous, intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eye-drops), including buccally and sublingually, transdermally, through an inhalation spray.

Regardless of the route of administration selected, the composition according to the invention is formulated into pharmaceutically acceptable dosage forms such as described herein or by other conventional methods known to those of skill in the art.

The expression "effective amount", also referred to as "therapeutically effective amount", of an active agent refers to the amount necessary to elicit the desired biological response. As will be appreciated by those of ordinary skill in this art, the effective amount of an agent may vary depending on such factors as the desired biological endpoint, the agent to be delivered, the composition of the encapsulating matrix, the target tissue, and the like.

The term "combination" is used in its broadest sense and means that a subject is administered at least two agents. More particularly, the term "in combination" refers to the concomitant administration of two (or more) active agents for the treatment of, e.g., a single disease state. As used herein, the active agents may be combined and administered in a single dosage form, may be administered as separate dosage forms at the same time, or may be administered as separate dosage forms that are administered alternately or sequentially on the same or separate days. In some embodiments of the presently disclosed subject matter, the active agents are combined and administered in a single dosage form. In some embodiments, the active agents are administered in separate dosage forms (e.g., wherein it is desirable to vary the amount of one but not the other). The single dosage form may include additional active agents for the treatment of the disease state.

According to different embodiments, the composition according to the invention can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of two (or more) agents can be varied so long as the beneficial effects of the combination of these agents are achieved. Accordingly, the phrase "in combination with" refers to the administration of a presently disclosed composition and, optionally, additional agents either simultaneously, sequentially, or a combination thereof. Therefore, a subject administered a combination of a presently disclosed composition and, optionally, additional agents can receive a presently disclosed composition and, optionally, additional agents at the same time (i.e., simultaneously) or at different times (i.e., sequentially, in either order, on the same day or on different days), so long as the effect of the combination of all agents is achieved in the subject.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered at a time just prior to an electroporation ablation procedure.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Qa/QA + Qb/QB = \text{Synergy Index (SI)}$$

wherein:

QA is the concentration of a component A, acting alone, which produced an end point in relation to component A;

Qa is the concentration of component A, in a mixture, which produced an end point;

QB is the concentration of a component B, acting alone, which produced an end point in relation to component B; and Qb is the concentration of component B, in a mixture, which produced an end point.

Generally, when the sum of Qa/QA and Qb/QB is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher than what can be expected based on the observed activities of the individual components when used alone. Further, a "synergistically effective amount" of a component refers to the amount of the component necessary to elicit a synergistic effect in, for example, another therapeutic agent present in the composition.

In an aspect, the presently disclosed subject matter provides a pharmaceutical composition and optionally, additional agents, alone or in combination with one or more additional therapeutic agents in admixture with a pharmaceutically acceptable excipient.

More particularly, in an aspect, the presently disclosed subject matter provides a pharmaceutical composition and, optionally, additional agents and a pharmaceutically acceptable carrier.

In an aspect, in therapeutic and/or diagnostic applications, the agents of the disclosure are administered systemically and delivered prior to an electroporation ablation procedure.

Use of pharmaceutically acceptable inert carriers to formulate the agents herein disclosed for the practice of the disclosure into dosages suitable for systemic administration is also within the scope of the disclosure.

Pharmaceutical compositions suitable for use in the present disclosure include compositions wherein the active ingredients are contained in an effective amount to achieve their intended purpose. Determination of the effective amounts is well within the capability of those skilled in the art, especially in light of the detailed disclosure provided herein. Generally, the agents according to the disclosure are effective over a wide dosage range. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

According to preferred embodiments of the invention, the non-thermal ablative energy is electroporation energy, or Irreversible Electroporation (IRE) energy.

Advantageously, the present invention contemplates the use of any source of electroporation energy.

In some embodiments of the invention, the electric field is placed adjacent to the target tissue (e.g., cardiac tissue) to be treated.

In some embodiments of the invention, the electric field energy is applied using an ablation catheter. In some embodiments, the ablation catheter comprises at least one electrode at the tip and a catheter body. In some embodiments, the electrode(s) of the catheter (e.g., ablation catheter, mapping catheter, ultrasound catheter, etc.) comprise(s) an electrode delivery component that is used to guide the electric field to the target tissue (e.g., cardiac tissue) to be ablated. In some embodiments, the electric field energy applied is between 250 V and 4100 V.

In some embodiments, the electroporation energy is applied using a catheter with at least one conductive electrode. In some embodiments, the electroporation catheter comprises a force-adjusting irrigated tip. In some embodiments, the electroporation catheter comprises a non-irrigated electroporation electrode catheter. In some embodiments, the electroporation catheter comprises a magnetic tip. In some embodiments, the electroporation catheter comprises a force-maintenance tip to maintain the conductive electrode in constant pressure against the moving heart wall.

Those skilled in the art will appreciate that the amount of electroporation energy applied in any particular situation may vary depending on a number of factors, including the target tissue to be ablated. In some embodiments, the electroporation energy applied is between 400 Volts and 5000 Volts. In some embodiments, the electroporation energy applied is between 2000 Volts and 4000 W.

According to an embodiment of the invention, the step b) of delivering non-thermal ablative energy to the target tissue to be ablated is carried out by means of an ablation equipment (1000) and said step b) comprises applying electric voltage signals (S, Sa, Sb, Va, Vb) to a plurality of electrodes (3, 30, 31) of said ablation equipment (1000), wherein each of said electric voltage signals (S, Sa, Sb, Va, Vb) is a sinusoidal wave.

According to an embodiment of the invention, said ablation equipment (1000) comprises an ablation catheter (1) and a single power source (4), wherein said ablation catheter (1) comprises:

a catheter elongated shaft (13) comprising at least an elongated shaft distal portion (17);

said catheter elongated shaft (13) comprising a flexible body (27) to navigate through body vessels (28);

said ablation catheter (1) further comprising a shaft ablation assembly (20) disposed at said elongated shaft distal portion (17);

said shaft ablation assembly (20) comprising at least said a plurality of electrodes (3, 30, 31) fixedly disposed at said elongated shaft distal portion (17);

all electrodes of said at least a plurality (3, 30, 31) being electrically connected to the single power source (4), said single power source (4) being configured to generate said sinusoidal electric voltage signals (Sa, Sb, Va, Vb) to energize each electrode for delivering the non-thermal energy to the target region of tissue to be ablated.

According to an embodiment of the invention, the single power source (4) is configured to supply at least a first (30) and a second (31) electrodes (30, 31) that are adjacent to each other on said ablation catheter (1), with sinusoidal electric voltage signals in phase with each other or out of phase with each other to generate a unipolar electric field and/or a bipolar electric field for delivering the non-thermal energy to the tissue (41) to be treated.

According to an embodiment of the invention, the single power source (4) is configured to supply the at least a first (30) and a second (31) electrodes with a first (Sa) and a second (Sb) sinusoidal electric voltage signals, respectively, the first (Sa) sinusoidal electric voltage signal having a phase difference (1) with the second (Sb) sinusoidal electric voltage signal equal to 0 degrees to generate a unipolar electric field from each of said first (30) and second (31) electrodes to a patient return electrode (5) for delivering unipolar non-thermal energy only to the tissue (41) to be treated.

According to an embodiment of the invention, the single power source (4) is configured to supply the at least a first (30) and a second (31) electrodes with a further first (Va) and a further second (Vb) sinusoidal electric voltage signals, respectively, the further first (Va) sinusoidal electric voltage signal having a phase difference (1) with the further second (Vb) sinusoidal electric voltage signal that can be varied from 0 degrees to 180 degrees to generate both a unipolar electric field from each of said first (30) and second (31) electrodes to a patient return electrode (5) and to generate a bipolar electric field between said first (30) and second (31) electrodes for delivering simultaneously unipolar and bipolar non-thermal energy to the tissue (41) to be treated.

According to an embodiment of the invention, the phase difference (1) between said further first (Va) and further second (Vb) sinusoidal electric voltage signals is 180 degrees to generate a bipolar electric field between said first (30) and second (31) electrodes for delivering bipolar non-thermal energy only to the tissue (41) to be treated.

According to an embodiment of the invention, a phase difference (1) between said further first (Va) and further second (Vb) sinusoidal electric voltage signals is 90 degrees to generate a bipolar electric field between said first (30) and second (31) electrodes which is double the unipolar electric field generated from each of said first (30) and second (31) electrodes to the patient return electrode (5).

According to an embodiment of the invention, a peak-to-peak mean amplitude of each sinusoidal electric voltage signal (Sa, Sb, Va, Vb) is in the range of 500 V to 5000 V, preferably the peak-to-peak mean amplitude is 3500 V.

According to an embodiment of the invention, the single power source (4) is configured to supply the at least a first (30) and a second (31) electrodes with sinusoidal electric voltage signals to generate alternatively a unipolar electric field or a bipolar electric field by time division multiplexing for delivering the non-thermal energy to the tissue (41) to be treated.

According to an embodiment of the invention, said single power source (4) comprises a single control unit (200) and a power unit (201) for generating said electric voltage signals (Sa, Sb, Va, Vb), wherein said power unit (201) is electrically connected to all electrodes of said plurality of electrodes (3, 30, 31).

According to an embodiment of the invention, said first (Sa) and second (Sb) sinusoidal electric voltage signals "in phase" are supplied to the at least first (30) and second (31) electrodes during a first voltage delivery time interval (T1), and the single control unit (200) is configured to drive the power unit (201) to modify the duration of said first voltage delivery time interval (T1) to change the level of the unipolar non-thermal energy delivered to the tissue (41) to be treated.

According to an embodiment of the invention, said further first (Va) and further second (Vb) sinusoidal electric voltage signals "out of phase" are supplied to the at least first (30) and second (31) electrodes during a second voltage delivery time interval (T2), and the single control unit (200) is configured to drive the power unit (201) to modify the duration of said second voltage delivery time interval (T2) to change the level of the unipolar and/or unipolar and bipolar non-thermal energy delivered to the tissue (41) to be treated.

According to an embodiment of the invention, the single control unit (200) is configured to drive the power unit (201) to modify the frequencies of said sinusoidal electric voltage signals (Sa, Sb, Va, Vb) to change the level of the unipolar and/or unipolar and bipolar non-thermal energy delivered to the tissue (41).

According to an embodiment of the invention, said power unit (201) is driven by the single control unit (200) to change the electric energy level associated to the voltage signals (Sa, Sb, Va, Vb) to be supplied to the electrodes (3, 30, 31) to switch from the non-thermal energy to a thermal energy, particularly Radio Frequency, RF, and vice versa.

The presently disclosed subject matter contemplates treating any condition, disease, or disorder in which augmented electroporation ablation of a target tissue in accordance with the compositions and methods disclosed herein would be desirable.

Accordingly, in an aspect, the presently disclosed subject matter provides for a method for treating a subject in need of augmented ablation of target tissue, the method comprising: (a) performing a presently disclosed method for augmenting electroporation ablation of a target tissue in the subject; and (b) applying electroporation to the target tissue in the subject, thereby treating the subject in need of augmented ablation of the target tissue.

In an embodiment of the invention, the target tissue to be ablated comprises cardiac tissue (e.g., myocardial tissue). In an embodiment, the target tissue comprises arrhythmogenic myocardial tissue. In an embodiment, the target tissue comprises myocardial scar or infiltrate. In an embodiment, the target tissue comprises solid tumor tissue. In an embodiment, the target tissue is not tumor tissue. In an embodiment, the target tissue is not solid tumor tissue. In an embodiment, the target tissue comprises a neurologic tissue responsible for seizures.

In a further aspect, the present invention relates to the above disclosed method for the treatment of a cardiac arrhythmia. In a preferred embodiment, the present invention provides for a method for treating a cardiac arrhythmia in a subject in need thereof, the method comprising: (a) performing a presently disclosed method for augmenting electroporation ablation of a target cardiac tissue in the subject; and (b) applying electroporation ablative energy to the target cardiac tissue in the subject, thereby treating the cardiac arrhythmia in the subject.

According to different embodiments, the cardiac arrhythmia is selected from the group consisting of atrial fibrillation, premature atrial contractions, wandering atrial pacemaker, multifocal atrial tachycardia, atrial flutter, supraventricular tachycardia, tachycardia selected from the group consisting of atrial tachycardia, atrioventricular nodal reentrant tachycardia, and atrioventricular reciprocating tachycardia, junctional rhythm, junctional tachycardia, premature junctional contraction, premature ventricular contractions, accelerated idioventricular rhythm, monomorphic ventricular tachycardia, polymorphic ventricular tachycardia, ventricular fibrillation, heart blocks, long QT syndrome, Brugada syndrome, catecholaminergic polymorphic ventricular tachycardia, arrhythmogenic right ventricular dysplasia, dilated cardiomyopathy, cardiomyopathy due to prior myocardial infarction, and abnormal Purkinje potentials leading to ventricular arrhythmias including electrical storms; and combinations thereof.

According to particular embodiments, the subject: (i) has a pacemaker; and/or (ii) has an implantable cardiac defibrillator; and/or (iii) is selected for treatment of a cardiac arrhythmia selected from the group according to the previous paragraph.

In some embodiments, the subject has comorbidity (e.g. other heart diseases such as heart failure).

In one aspect, the present invention relates to the above disclosed method for the treatment of proximal, persistent or long-standing persistent atrial fibrillation in a subject in need thereof, wherein:

an ablation equipment (1000) according to any one of the above described embodiments is provided, the ablation catheter (1) is placed in the coronary sinus of the subject, such as to deliver the non-thermal ablative energy to the target tissue to be ablated, and the ablation catheter (1) is placed in the left or right atrium to deliver the non-thermal ablative energy to the target tissue to be ablated, wherein the target tissue to be ablated include: fascicles around a pulmonary vein, and/or the left atrial roof, and/or the mitral isthmus.

In one aspect, the present invention relates to the above disclosed method for the treatment of atrial flutter in a subject in need thereof, wherein:

an ablation equipment (1000) according to any one of the above described embodiments is provided, the ablation catheter (1) is placed in one or more locations in the right atrium of the heart to achieve bi-directional block by delivering non-thermal ablative energy to the target tissue to be ablated.

In one aspect, the present invention relates to the above disclosed method for the ablation of tissue in the right atrium of the heart, wherein:

an ablation equipment (1000) according to any one of the above described embodiments is provided, the ablation catheter (1) is placed in one or more locations in the right (and/or left) atrium of the heart (43);

lesions are created between the superior vena cava and the inferior vena cava, and/or the coronary sinus and the inferior vena cava, and/or the superior vena cava and the coronary sinus by delivering non-thermal energy to the target tissue to be ablated.

In one aspect, the present invention relates to the above disclosed method for the treatment of sinus node tachycardia in a subject in need thereof, wherein:

an ablation equipment (1000) according to any one of the above described embodiments is provided, the ablation catheter (1) is placed in one or more locations in the right (and/or left) atrium of the heart (43);

the sinus node is ablated by delivering non-thermal ablative energy.

In one aspect, the present invention relates to the above disclosed method for the treatment of ventricular tachycardia in a subject in need thereof, comprising the following steps:

providing an ablation equipment (1000) according to any one of the above described embodiments, placing the ablation catheter (1) in the left or right ventricles of the heart (43);

inducing ventricular tachycardia by delivering pacing energy, and ablating tissue to treat the subject by delivering non-thermal energy to the target tissue to be ablated.

It is a purpose of this invention, in certain embodiments, to provide a method for augmenting electroporation ablation of target tissues (e.g., cardiac tissue) using magnetically guided nanoparticles.

In an aspect, the presently disclosed subject matter provides a method for augmenting electroporation ablation of target cardiac tissue using metallic nanoparticles that are magnetically guided to a target cardiac tissue to be ablated. Advantageously, ablation of cardiac tissue treated with metallic nanoparticles augments local electroporation, for example, by increasing ablation lesion size, providing a greater reduction in electrical conductivity, and/or increased non-thermal conductivity in target cardiac tissue to be non-thermally ablated. Metallic nanoparticles can be vascularly guided to a target cardiac tissue electroporation ablation site for precise targeting of myocardial tissues. It is believed that augmented electroporation ablation of target cardiac tissue using magnetically nanoparticles can be used to increase electroporation effectiveness to treat a variety of cardiac diseases (e.g., cardiac arrhythmias).

In an aspect, the presently disclosed subject matter provides a method for augmenting electroporation ablation of a target cardiac tissue in a subject in need thereof, the method comprising: (a) administering an effective amount of a composition comprising metallic nanoparticles to a subject; (b) using the vascular system to deliver the metallic nanoparticles to a target cardiac tissue to be ablated in the subject; and (c) applying electroporation energy to the target cardiac tissue in the presence of the metallic nanoparticles delivered to the target cardiac tissue, thereby augmenting electroporation ablation of the target cardiac tissue in the subject.

In an embodiment, augmenting electroporation ablation comprises administering to the subject an effective amount of a composition comprising metallic nanoparticles, and using a magnetic field to guide the metallic nanoparticles to the target tissue (e.g., cardiac tissue) to be ablated, thereby augmenting ablation of the target tissue in the subject. In an embodiment, the ablative energy comprises electroporation energy applied the target tissue (e.g., cardiac tissue) in the presence of the metallic nanoparticles guided to the target cardiac tissue.

In an embodiment, augmenting electroporation ablation comprises: (i) administering to the subject an effective amount of an agent that causes significant changes in cell membrane permeability, which leads to a cell apoptotic process, with depletion of ATP and increased intracellular calcium concentrate, thereby sensitizing the target cardiac tissue to the electroporation ablative energy, and (ii) administering to the subject an effective amount of a composition comprising metallic nanoparticles, and using a magnetic field to guide the metallic nanoparticles to the target cardiac tissue to be ablated, thereby augmenting electroporation ablation of the target cardiac tissue in the subject.

In an embodiment, augmenting electroporation ablation comprises administering to the subject an effective amount of a composition comprising metallic nanoparticles and at least one agent that causes significant changes in cell membrane permeability, which leads to a cell apoptotic process, with depletion of ATP and increased intracellular calcium concentrate by application of the electroporation ablative energy to the target cardiac tissue, and using a magnetic field to guide the composition comprising the metallic nanoparticles and at least one agent that causes significant changes in cell membrane permeability, which leads to a cell apoptotic process, with depletion of ATP and increased intracellular calcium concentrate, that modulates a protective and/or reparative cellular process induced in the target cardiac tissue by application of the electroporation ablative energy to the target cardiac tissue to be ablated, thereby augmenting ablation of the target cardiac tissue in the subject.

In some embodiments, the changes in cell membrane permeability, which leads to a cell apoptotic process, with depletion of ATP and increased intracellular calcium concentrate induced protective and/or reparative cellular process comprising a heat shock response process modulated by a heat shock protein (HSP), and the agent decreases the level and/or activity of a heat shock protein in the target tissue to be ablated.

In an aspect, the presently disclosed subject matter contemplates the use of any metallic nanoparticle that is capable of being delivered through the venous system via injection into veins and/or arteries to a target tissue when administered to a subject.

In an aspect, the presently disclosed subject matter contemplates delivering the metallic nanoparticles in any suitable delivery vehicle alone, or optionally together with at least one additional presently disclosed agent (e.g., at least one agent that modulates an apoptotic effect and/or ATP levels induced in a target tissue by application of electroporation ablative energy to the target tissue). In some embodiments, the delivery vehicle comprises liposomes.

It is to be understood that the any agent described herein can be included in the composition comprising magnetic nanoparticles. In some embodiments, the composition further comprises at least one calcium agent that modulates apoptotic effect and/or ATP levels in a target tissue by application of an electroporation ablative energy to the target tissue. In some embodiments, at least one agent that modulates a protective and/or reparative cellular process induced in a target tissue by application of an ablative energy to the target tissue is encapsulated in liposomes. In some embodiments, the composition further comprises an agent that decreases the expression level and/or activity of a heat shock protein. In some embodiments, the composition further comprises at least one agent that induces apoptosis. In some embodiments, the composition further comprises sonosensitizers. In some embodiments, the composition further comprises inert metals compounds. In some embodiments, the composition further comprises biological response enhancers (e.g., in relationship to electroporation). In some embodiments, the composition further comprises adoptive immunotherapy agents when in the presence of electroporation. In some embodiments, the composition further comprises agents that induce cell differentiation when in the presence of electroporation (e.g., all-trans-retinoic acid). In some embodiments, the composition further comprises heavy metals (e.g., barium, gold, or platinum).

In some embodiments, the agent that modulates a protective and/or reparative cellular process induced in a target tissue by application of electroporation to the target tissue is quercetin, or an analog or derivative thereof. In some embodiments, the agent that decreases the expression level and/or activity of a heat shock protein is quercetin, or an analog or derivative thereof.

In some embodiments, the agent that modulates a protective and/or reparative cellular process induced in a target tissue by application of electroporation to the target tissue is 17-allyl amino geldanamycin (17-AAG), or an analog, derivative, or pro-drug thereof. In some embodiments, the agent that decreases the expression level and/or activity of a heat shock protein is 17-AAG, or an analog, derivative thereof, or pro-drug thereof. Exemplary pro-drugs of 17-AAG are described in U.S. Publication No. 2006/025270, which is incorporated herein by reference in its entirety. Exemplary analogs or derivatives of 17-AAG include, without limitation.

In some embodiments, the agent that modulates a protective and/or reparative cellular process induced in a target tissue by application of electroporation to the target tissue is celestrol, or an analog or derivative thereof. In some embodiments, the agent that decreases the expression level and/or activity of a heat shock protein is celestrol, or an analog or derivative thereof.

In some embodiments, the metallic nanoparticles are functionalized with at least one additional agent (e.g., an agent disclosed herein), optionally via a linker. For example, the metallic nanoparticles can be functionalized with at least one agent that modulates a protective and/or reparative cellular process induced in a target tissue by application of electroporation to the target tissue. In some embodiments, the metallic nanoparticles are functionalized with at least one agent that decreases the expression level and/or activity of a heat shock protein via a slight increase in the thermally labile linking group or as a direct result of electroporation that disintegrates or breaks and releases the at least one agent. In this way, the metallic nanoparticles can be magnetically guided to a target tissue (e.g., cardiac tissue) and upon application of electroporation energy, the electroporation/slight thermally labile linking group breaks and locally releases the at least one agent (e.g., that decreases the expression level and/or activity of a heat shock protein) in the target tissue to be exposed to electroporation, thereby augmenting electroporation of the target tissue while locally administering the at least one agent to the target tissue.

In an aspect, the presently disclosed subject matter contemplates the use of any magnetic field that is capable of exhibiting a sufficient pound pull force to guide the magnetic particles to a target tissue to be ablated. In some embodiments, the magnetic field is generated by a magnet that exhibits a pound pull force of between 0.001 and 1000. Those skilled in the art will appreciate that the pound pull force of any particular magnet used may vary depending on several factors, for example, based on the distance and placement of the magnet relative to the magnetic nanoparticles and target tissue. In some embodiments, the magnet has a pound pull force of about 310.

In some embodiments, the magnet is placed adjacent to the target cardiac tissue to be ablated. For example, to guide a composition comprising metallic nanoparticles administered to a subject to a target cardiac tissue, a magnet can be placed outside of the body in proximity to the chest cavity of the subject, to attract the composition comprising metallic nanoparticles to the target cardiac tissue in the subject. In some embodiments, the magnet is placed adjacent to the tip of a mapping catheter that is not used to ablate the target tissue. In some embodiments, the magnet is placed within the tip of a mapping catheter that is not used to ablate the target tissue. In some embodiments, the magnet is incorporated into an ultrasound catheter (e.g., near the catheter tip). In some embodiments, the magnet comprises a component of a standalone magnetic catheter. In some embodiments, the magnet comprises a magnet incorporated into a tip of an ablation catheter. In some embodiments, the magnet comprises an electromagnet. In some embodiments, the electromagnet is capable of turning on and off. In some embodiments, the magnet comprises an electromagnet in an electroporation energy catheter wherein the electromagnet is located in the same tip that emits the electroporation energy.

In some embodiments, the magnet is a rare-earth magnet. In some embodiments, the magnet is a neodymium magnet.

Advantageously, the method according to the present invention provides for selective ablation of a target tissue.

It is a purpose of this invention, in certain embodiments, to provide a combination treatment system that has at least one energy delivery device, or ablation catheter 1, and at least one power or energy or power source, or single power source 4, that is capable of providing non-thermal energy, particularly IRE energy, to the energy delivery device.

It is a purpose of this invention, in certain embodiments, to provide a method which involves providing application of Irreversible Electroporation (IRE) energy to ablate and/or treat tissue 41, such as to perform a treatment of tissue with a non-thermal form to effectively non-thermally ablate tissue. The method can involve providing at least one energy source which comprises at least a non-thermal energy source 4 which is powered by a rechargeable battery or by an AC wall source. The method can further comprise positioning via a catheter 1 at least a portion of the at least one catheter 1 within a desired region of a heart 43 or organ 44, selectively coupling the at least one catheter 1 and electrodes 3, 30, 31 to the non-thermal energy source 4, selectively energizing the non-thermal energy source 4 to apply non-thermal therapy from the non-thermal energy source to at least a portion of the desired region to ablate at least a portion of the desired region, and withdrawing the at least one catheter 1 from the desired region.

As such, in certain embodiments, the present invention utilizes sinusoidal wave in such a way as to deliver timed high voltage electrical energy which causes the same cell effect similar to that of square-wave pulsed electric field ablation.

The therapy targets the tissue with therapy being delivered in the range of microseconds to milliseconds that can lead to near non-thermally produced defects in the cell membrane that are nanoscale in size, without stimulating the cardiac muscle, without causing un-wanted arrhythmias, muscles stimulations and with a high level of selectivity and patient safety as compared to the negative effects of DC or square waves.

In such embodiments, the Sinusoidal wave Irreversible Electroporation (IRE) leads to a disruption of homeostasis of the cell membrane, thereby causing irreversible cell membrane permeabilization which induces cell necrosis, without raising the temperature of the tissue ablation zone. During IRE ablation, connective tissue and scaffolding structures are spared, thus allowing the surrounding organs, structures, blood vessels, and connective tissue to remain intact. With near non-thermal ablation via irreversible electroporation, cell death is mediated through a non-thermal mechanism, so the heat sink problem associated with many ablation techniques is nullified. Therefore, the invention has the advantages of IRE to allow focused treatment with tissue sparing and without thermal effects.

According to alternative embodiments, there are also advantages of utilizing thermal ablation during treatment procedures. Prior to the disclosure of this invention, an invention had not been proposed that could solve the problems of non-thermally ablating a target region of cardiac or organ 44 tissue 41 using a sinusoidal wave, while maintaining integrity of the surrounding tissue, and effectively switching to a device for effectively thermally ablating tissue along the ablation track. In certain proposed embodiments, an energy delivery device or catheter 1 can be utilized that is powered by a single energy source 4 that is capable of application of energy in various forms, and subsequently ablating a tissue track during a medical procedure for the treatment of arrhythmias using the same energy delivery device 1 that can be powered by a different source (AC or Battery) of energy from the same generator 4, to maximize procedure efficiencies. As indicated, Sinusoidal IRE provides advantages for non-thermal cell death without cardiac muscle stimulation experienced in square-waves Pulsed Electric Field (PEF).

According to alternative embodiments, it is a purpose of this invention, to provide a high voltage sinusoidal wave electric field treatment system that has at least one energy/power delivery source 4 for each single or paired electrode (s) 3, 30, 31 on the catheter 1. The at least one power or energy or power source 4 is capable of providing a sinusoidal IRE energy to the catheters electrode(s) 3, 30, 31.

The at least one energy delivery device 1 can be a unipolar/bipolar, or a monopolar/bipolar device. The system can have at least one manual or automatic switching device for switching the energy or power modes utilized between any one or more electrodes 3, 30, 31 or any combination (and adjustable ratios) in between full monopolar and/or/unipolar and full biphasic and/or bipolar.

According to alternative embodiments, it is a purpose of this invention to provide a combination treatment system that has at least one energy delivery device 1 and at least one power or energy or power source 4 that is capable of providing sinusoidal IRE energy and thermal energy to the energy delivery device. The system can either switch full monopolar and/or/unipolar and full biphasic and/or bipolar, combine full monopolar and/or/unipolar and full biphasic and/or bipolar.

According to alternative embodiments, it is a further purpose of this invention to provide a method that involves using non-thermal Sinusoidal IRE energy and thermal energy to effectively ablate target regions of tissue 41. The method involves positioning at least one energy delivery device 1 that is coupled to a single power source 4 within a target region of a tissue, applying Sinusoidal IRE energy from the power source 4 to the energy delivery device 1 which is used to ablate a target region of tissue 41, while preventing damage to surrounding structures, then switching from Sinusoidal IRE energy to thermal energy using the same power source, and positioning the energy delivery device 1 while ablating said tissue with thermal energy, such as RF energy, to allow for focal tissue ablation and the safe energy delivery used during the treatment procedure, while among other things, coagulating tissue and preventing bleeding.

According to a preferred embodiment, a constant voltage source Vcc is utilized for all singular or pairs of Pulsed Electric Field (electrodes) and adjustment of the phase angle of the applied (sinusoidal wave) voltage produces different ratios of simultaneous and/or cumulative unipolar and bipolar energy delivered such as to create non-thermal varied length and depth lesions in the tissue 41 of a patient.

According to another preferred embodiment, a constant voltage source is utilized for all pairs of IRE outputs 202 and adjustment of the phase relationship between source produces different ratios of simultaneous and/or cumulative unipolar and bipolar energy delivered such as to create tissue selective non-thermal varied length and depth lesions in the tissue 41 of a patient. In this embodiment, the pulsed duration used during voltage delivery may be fixed, or alternatively it may be varied such as a configuration in which a minimal pulse time is used which incrementally increases to reach a tissue selective non-thermal target tissue ablation. In this embodiment, the phase shift may be fixed, such as fixed at 90° or 180° phase shift to create the bipolar energy.

In yet another preferred embodiment, varying the pulse duration "on" time of bipolar and/or unipolar voltage delivery is utilized for all pairs of IRE outputs and adjustment of this duration produces different cumulative unipolar and bipolar IRE energy delivered such as to create varied tissue selective non-thermal length and depth lesions in the tissue of a patient. The phase difference (1) between the bipolar fields (or combined unipolar-bipolar fields) to unipolar fields may be adjusted to achieve a desired voltage of bipolar-unipolar ratio. Alternatively or additionally, the pulse duration within the bipolar fields (or combined unipolar-bipolar fields) and the unipolar fields may be adjusted to achieve the desired power level and/or bipolar-unipolar ratio to the tissue. Alternatively or additionally, the fields length of the bipolar fields (or combined unipolar-bipolar fields) and the unipolar fields may be adjusted.

The IRE generators of the present invention may employ one or more energy delivery algorithms to control voltage delivery. In a preferred embodiment, an algorithm of the present invention can provide voltage at a fixed level, such as a maximum voltage, changing the number of pulses and pulse duration until the tissue to be ablated is no longer electrically conductive. For tissue that is conductive, not yet thoroughly ablated, the system will provide visual feedback to the operator. Target tissue ECG levels and/or threshold bio signals are monitored by the system but also adjustable by an operator of the system (manual or automatic). In another preferred embodiment, an algorithm employs a main control loop based on a power absorption differential analysis and a secondary control loop based on an ECG signal comparison to baseline.

In another embodiment, the system and method include closed loop voltage delivery for each IRE output including a PID control loop which receives information from an electrode on the ablation catheter such as to provide closed loop energy delivery based on measured and analyzed bio-signals. Voltage delivery may comprise delivery of multiple pulses that are configured to improve tissue selective non-thermal lesion creation efficiency, safer ablations over RF or square wave supplies. Selected durations allow delivery of high peak powers while providing precise timed pulses such as to reduce (e.g. prevent) heating the tissue and/or avoid causing harmful effects to non-targeted tissue.

In addition, pulsed duration control simplifies design and control of multiple IRE outputs utilizing different phase angles. Durations cycle energy delivery also improves data acquisition as data can be acquired during the off portion of the pulse (i.e., during the IRE "off time"). The system and method including bio-signal acquisition provide fast, accurate and electrically-isolated ECG, Bio-signals acquisition for all electrodes. Each catheter electrode may include a small mass filter/digital converter. The system and method provide safe, controlled energy delivery.

In yet another preferred embodiment, the IRE generator includes a first set of ablation parameters that are utilized when a first form of ablation catheter is attached to the IRE outputs and a second set of ablation parameters that are utilized when a second form of ablation catheter is attached to the IRE outputs.

In yet another preferred embodiment, the IRE generator includes an improved ECG interface for connecting the IRE outputs to an ECG diagnostic device. When one or more ablation catheters 1 are attached to the IRE generator 4, the electrodes of the ablation catheter are electrically attached to the IRE outputs of the IRE generator. The IRE generator is powered by battery, the battery is not connected to the wall's AC power supply. This means, the IRE generator does not have to filter the AC noise from the wall, the IRE battery powered generator is fully isolated. This will improve ECG signals coming from the patient due to no AC noise/interference.

According to another aspect of the invention, a system for performing a tissue selective non-thermal ablation procedure is described. In a preferred embodiment, one or more non-thermal ablation catheters are provided with an IRE generator of the present invention. In another preferred embodiment, a wireless remote control is provided with the IRE generator of the present invention.

According to alternative embodiments, a system for selectively ablating tissue 41 is provided herein that has at least one energy source 4, at least one catheter 1, and a means for selectively coupling the catheters electrodes 3, 30, 31 to either ground or to each other. The means for selectively energizing the electrodes to at least one energy source can apply sinusoidal voltage pulses energy to at least a portion of the desired region to ablate at least a portion of the desired region. The means for selectively energizing the electrodes can energize any one or combinations of the catheter electrodes.

A unique multi-electrode and multi-functional ablation catheter 1 and ablation catheter systems and methods are provided which map and ablate myocardial tissue within the heart chambers of a patient. Any electrocardiogram signal site (e.g. a site with aberrant signals) or combination of multiple sites that are discovered with this placement may be ablated. In alternative embodiments, the ablation catheters and systems may be used to treat non-cardiac patient tissue, such as tumor tissue, renal artery nerves, etc.

According to an aspect of the invention, a probe or an ablation catheter 1 for performing a medical procedure on a patient is provided. The ablation catheter 1 comprises an elongated shaft 13 with a proximal portion 14 including a proximal end 15 and a distal end 16, and a distal portion 17 with a proximal end 18 and a distal end 19. The elongated shaft further comprises a shaft ablation assembly 20 and a distal ablation assembly 21 configured to deliver energy, such as Irreversible Electroporation (IRE) energy to tissue. The shaft ablation assembly 20 is proximal to the distal end 19 of the distal portion 17, and includes at least one shaft ablation element 3, 30, 31 fixedly or removable attached to the shaft and configured to deliver ablation energy to tissue 41. The distal ablation assembly 21 is at the distal end of the distal portion and includes at least one tip ablation element 23 configured to deliver ablation energy to tissue.

According to alternative embodiments, the distal portion of the catheter 1 is fabricated to be in a forward facing circular configuration and can be deflected in one or more directions, in one or more deflection shapes and geometries 24.

The deflection geometries 24 may be similar or symmetric deflection geometries, or the deflection geometries may be dissimilar or asymmetric deflection geometries. The shaft 13 may include one or more steering wires configured to deflect the distal portion in the one or more deflection directions. The catheter deflection can also occur by placing or removing a shape setting center mandrel 26. The elongated shaft 13 may include a difference in the stiffness of the shaft along its length. The elongated shaft may include a shape setting mandrel 26 within the shaft, the shape setting mandrel configured to perform or enhance the deflection (steering and shape) of the distal portion 17, such as to maintain deflections in a single plane. The shaft may include variable material properties such as an asymmetric joint between two portions, an integral member within a wall or fixedly attached to the shaft, a variable braid, or other variation used to create multiple deflections, such as deflections with asymmetric deflection geometries.

In another preferred embodiment, the location on the catheter that transitions from circular to linear is a mechanical elbow/wrist. It can be articulated from the proximal end of the catheter 1 such as to cause the distal section to go from straight or curved on a single plane, to straight or curved on a 3D plane or perpendicular to the shaft. The mechanical elbow/wrist can be heat activated.

In another preferred embodiment, the distal ablation assembly 21 may be fixedly attached to the distal end of the distal portion, or it may be advanceable from the distal shaft, such as via a control port. The distal ablation assembly 21 may comprise a single ablation element, such as a single mandrel electrode, or multiple ablation elements 32. The distal ablation assembly may include a shape setting mandrel carrier assembly of ablation elements, and the shape setting mandrel carrier assembly may be changeable from a compact geometry to an expanded geometry, such transition caused by advancement and/or retraction of a control shaft.

The shaft ablation assembly 20 may include a single ablation element or multiple ablation elements 3, 30, 31, for example five to ten ablation elements fixedly attached to the shaft or shape setting mandrel. The ablation elements may have a profile that is flush with the surface of the shaft, or the shaft between the electrode elements outer diameter is slightly smaller than the diameter of the ablation electrodes such that the distal end of the catheter is more flexible.

The ablation elements of the present invention can deliver one or more forms of energy, for example RF and/or Irreversible Electroporation (IRE) energy. The ablation elements may have similar or dissimilar construction, and may be constructed in various sizes and geometries. The ablation elements may include one or more thermocouples, such as two thermocouples mounted 90° from each other on the inside of an ablation element. The ablation elements may include means of dissipating heat, such as increased surface area. In a preferred embodiment, one or more ablation elements is configured in a tubular geometry, and the wall thickness to outer diameter approximates a 1:15 ratio. In another preferred embodiment, one or more ablation elements is configured to record, or map electrical activity in tissue such as mapping of cardiac electrograms. In yet another preferred embodiment, one or more ablation elements is configured to deliver pacing energy, such as to deliver energy to pace the heart of a patient.

The ablation catheters comprising electrodes 3, 30, 31 of the present invention may be used to treat one or more medical conditions by delivering ablation energy to tissue 41. Conditions include an arrhythmia of the heart, cancer, and other conditions in which removing or denaturing tissue improves the patient's health.

According to another aspect of the invention, a kit 300 of ablation catheters is provided. A first ablation catheter 1 has a distal portion which can be deflected in at least two symmetric geometries. A second ablation catheter 1' has a distal portion which can be deflected in at least two asymmetric geometries.

According to another aspect of the invention, a method of treating proximal, persistent or long-standing persistent atrial fibrillation is provided. An ablation catheter 1 included in the equipment of the present invention may be placed in the coronary sinus of the patient, such as to map electrograms and/or ablate tissue, and subsequently placed in the left or right atrium to map electrograms and/or ablate tissue. The ablation catheter 1 may be placed to ablate one or more tissue locations including but not limited to: fascicles around a pulmonary vein; the left atrial roof, and the mitral isthmus.

According to another aspect of the invention, a method of treating atrial flutter is provided. An ablation catheter 1 included in the equipment of the present invention may be used to achieve bi-directional block, such as by placement in one or more locations in the right atrium of the heart.

According to another aspect of the invention, a method of ablating tissue in the right atrium of the heart is provided. An ablation catheter 1 included in the equipment of the present invention may be used to: create lesions between the superior vena cava and the inferior vena cava; the coronary sinus and the inferior vena cava; the superior vena cava and the coronary sinus; and combinations of these. The catheter can be used to map electrograms and/or map and/or ablate the sinus node, such as to treat sinus node tachycardia.

According to another aspect of the invention, a method of treating ventricular tachycardia is provided. An ablation catheter 1 included in the equipment of the present invention may be placed in the left or right ventricles of the heart, induce ventricular tachycardia by delivering pacing energy, and ablate tissue to treat the patient.

According to another aspect of the invention, an ablation catheter with a first geometry larger than a second deflection geometry is provided via the shape setting mandrel. The ablation catheter is placed in the smaller second shape geometry to ablate one or more of the following tissue locations: left atrial septum; tissue adjacent the left atrial septum; and tissue adjacent the left atrial posterior wall. The ablation catheter is placed in the larger first geometry to ablate at least the circumference around the pulmonary veins.

According to another aspect of the invention, an ablation catheter 1 of the present invention is used to treat both the left and right atria of a heart. The catheter is configured to transition to a geometry with a first shape setting mandrel and/or deflection geometry and a second shape setting mandrel and/or deflection geometry, where the first geometry is different than the second geometry. The catheter is used to ablate tissue in the right atrium using at least the first geometry and also ablate tissue in the left atrium using at least the second geometry.

According to an aspect of the invention, a catheter for performing a medical procedure on a patient is provided. The catheter 1 comprises an elongated shaft 13 with a proximal portion including a proximal end and a distal end, and a distal portion with a proximal end and a distal end. The catheter further comprises a shape setting mandrel and/or deflection assembly configured to shape the distal portion in a first direction in a first geometry and a second direction in a second geometry, wherein the first and second geometries are different. The catheter further includes a functional element fixedly mounted to the distal portion.

Therefore, it is an object of the present invention to provide a method such as to meet the aforementioned needs and overcome the drawbacks mentioned above with reference to the solutions of the prior art. It is another object of the present invention to provide an ablation equipment 1000 having structural and functional features such as to meet the aforementioned needs to overcome the drawbacks mentioned above with reference to the solutions of the prior art.

These and other objects are achieved using ablation equipment for delivering non-thermal energy to treat target regions of tissue in organs. The ablation equipment can comprise an ablation catheter and a single power source. The ablation catheter can comprise a catheter elongated shaft comprising at least an elongated shaft distal portion. The catheter elongated shaft can comprise a flexible body to navigate through body vessels. The ablation catheter can further comprise a shaft ablation assembly disposed at the elongated shaft distal portion. The shaft ablation assembly can comprise at least a plurality of electrodes that are fixedly disposed at the elongated shaft distal portion. All the electrodes of the at least a plurality of electrodes can be electrically connected to the single power source. The single power source can be configured to generate electric voltage signals (Sa, Sb, Va, Vb) to energize each electrode for delivering the non-thermal energy to the tissue to be treated. Each of said electric voltage signals (Sa, Sb, Va, Vb) can be a sinusoidal wave, and the single power source can be configured to supply at least a first electrode and a second electrode (e.g. electrodes adjacent to each other on the ablation catheter) with sinusoidal electric voltage signals (e.g. in phase with each other and/or out of phase with each other) to generate a unipolar electric field and/or a bipolar electric field for delivering the non-thermal energy to the tissue to be treated. Methods of the present invention comprise a method for controlling at least a plurality of electrodes in an ablation equipment for delivering non-thermal energy to treat target regions of tissue, as described immediately hereabove and otherwise herein.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

Further features and advantages of the invention will become apparent from the description provided below of exemplary embodiment thereof, given by way of non-limiting example, with reference to the accompanying drawings, in which.

The same or similar elements are indicated in the drawings by the same reference numeral.

DESCRIPTION OF SOME PREFERRED EMBODIMENTS

Figure 1:
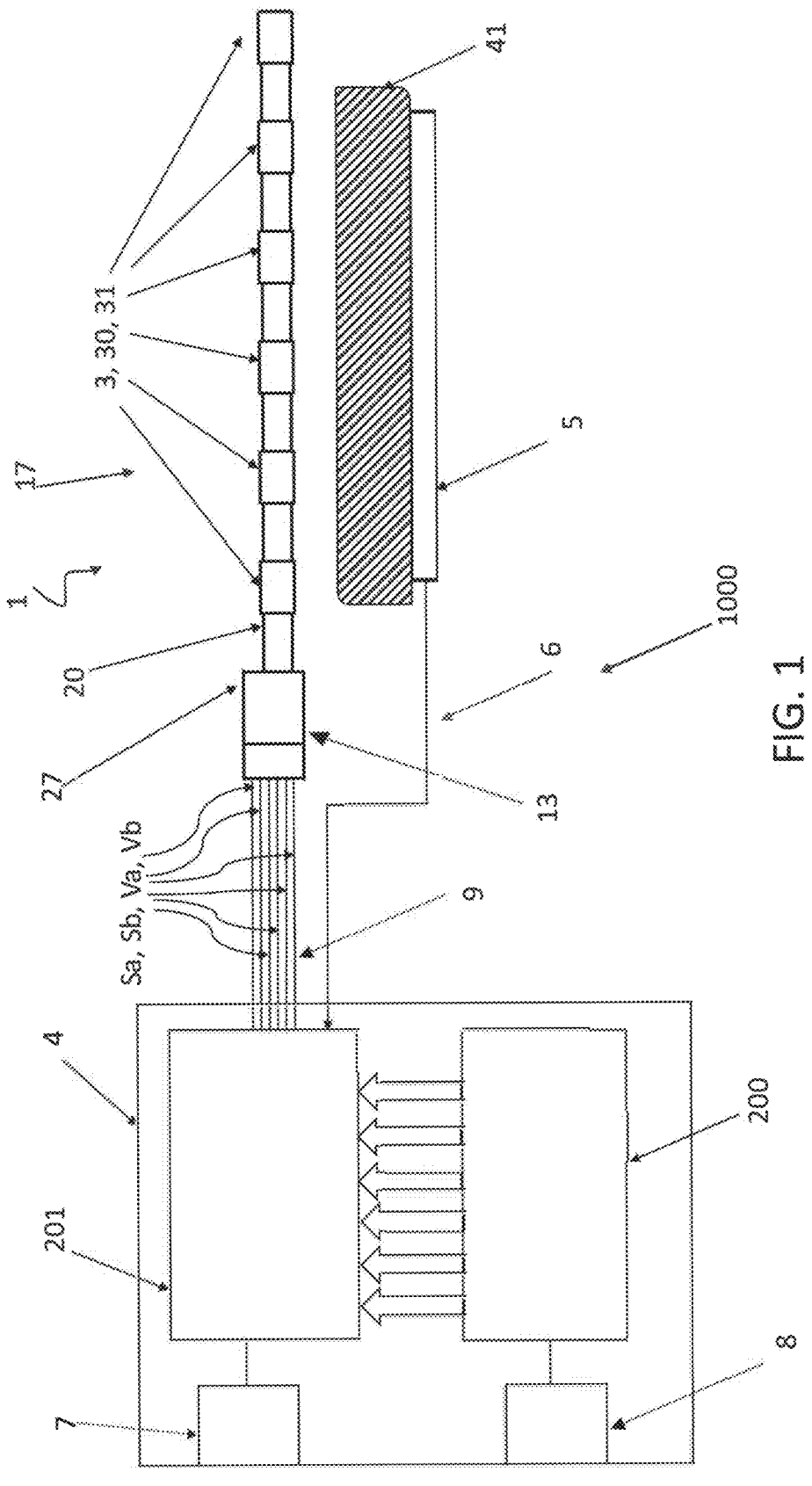
FIG. 1 shows schematically an ablation equipment for delivering non-thermal energy to treat target regions of tissue in organs according to the present invention, wherein the ablation equipment comprises an ablation catheter and a single power source.

The present invention can be understood more readily by reference to the following detailed description, examples, drawing, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

The term "distal" is understood to mean away from a medical practitioner and towards the body site at which the procedure is performed, and "proximal" means towards the medical practitioner and away from the body site.

In accordance with a general embodiment, with reference to FIGS. 1, 2, 3A-3B, 4, 5A-5B, an ablation equipment 1000 for delivering non-thermal energy to treat target regions of tissue 41 in organs 44, comprises an ablation catheter 1 and a single power source 4.

The ablation catheter 1 comprises a catheter elongated shaft 13 comprising at least an elongated shaft distal portion 17.

The catheter elongated shaft 13 comprises a flexible body 27 to navigate through body vessels 28.

The ablation catheter 1 further comprises a shaft ablation assembly 20 disposed at said elongated shaft distal portion 17. Said shaft ablation assembly 20 comprises at least a plurality of electrodes 3, 30, 31 fixedly disposed at said elongated shaft distal portion 17.

Particularly, the example of FIG. 1 shows six electrodes 3, 30, 31 fixedly disposed at said elongated shaft distal portion 17.

In a preferred embodiment, the biological tissue 41 to be treated is a cardiac tissue.

All electrodes of said at least a plurality 3, 30, 31 are electrically connected to the single power source 4, particularly with six wires 9.

The single power source 4 is configured to generate electric voltage signals Sa, Sb, Va, Vb to energize each electrode 3, 30, 31 for delivering the non-thermal energy to the tissue 41 to be treated, i.e. to apply voltage electric fields to the tissue 41 through the electrodes.

In addition, the electronic equipment 1000 comprises a further electrode 5 acting as a patient return electrode for the voltage electrical fields applied to the tissue 41. Particularly, this patient return electrode 5 or backplate is electrically connected to the single power source 4 through a respective return wire 6.

Advantageously, each of said electric voltage signals Sa, Sb, Va, Vb is a sinusoidal wave, and the single power source 4 is configured to supply at least a first 30 and a second 31 electrodes, that are adjacent to each other on the ablation catheter 1, with sinusoidal electric voltage signals in phase with each other or out of phase with each other to generate a unipolar electric field and/or a bipolar electric field for delivering the non-thermal energy to the tissue 41 to be treated.

In accordance with an embodiment, the non-thermal energy is IRreversible Electroporation, IRE, energy.

With the present invention, the Applicant proposes the use of an electric voltage signal Sa, Sb, Va, Vb for ablating the tissue 41 that consists of a sine-wave, in such a way as to deliver timed high voltage electrical energy which causes the same cell effect similar to that of square-wave pulsed electric field ablation.

In accordance with an alternative embodiment, the single power source 4 is configured to supply the at least a first 30 and a second 31 electrodes with a first Sa and a second Sb sinusoidal electric voltage signals, respectively. The first Sa sinusoidal electric voltage signal has a phase difference 1 with the second Sb sinusoidal electric voltage signal equal to 0 degrees to generate a unipolar electric field from each of said first 30 and second 31 electrodes to the patient return electrode 5 for delivering unipolar non-thermal energy only to the tissue 41 to be treated.

In accordance with an alternative embodiment, the single power source 4 is configured to supply the at least a first 30 and a second 31 electrodes with a further first Va and a further second Vb sinusoidal electric voltage signals, respectively. The further first Va sinusoidal electric voltage signal having a phase difference 1 with the further second Vb sinusoidal electric voltage signal that can be varied from 0 degrees to 180 degrees to generate both a unipolar electric field from each of said first 30 and second 31 electrodes to the patient return electrode 5 and to generate a bipolar electric field between said first 30 and second 31 electrodes for delivering simultaneously unipolar and bipolar non-thermal energy to the tissue 41 to be treated.

In accordance with an alternative embodiment, the phase difference 1 between said further first Va and further second Vb sinusoidal electric voltage signals is 180 degrees to generate a bipolar electric field between said first 30 and second 31 electrodes for delivering bipolar non-thermal energy only to the tissue 41 to be treated.

In accordance with an alternative embodiment, a phase difference 1 between said further first Va and further second Vb sinusoidal electric voltage signals is 90 degrees to generate a bipolar electric field between said first 30 and second 31 electrodes which is double the unipolar electric field generated from each of said first 30 and second 31 electrodes to the patient return electrode 5.

In accordance with an alternative embodiment, a peak-to-peak mean amplitude of each sinusoidal electric voltage signal Sa, Sb, Va, Vb is in the range of 500 V to 5000 V, preferably the peak-to-peak mean amplitude is 3500 V.

In accordance with an alternative embodiment, the single power source 4 is configured to supply the at least a first 30 and a second 31 electrodes with sinusoidal electric voltage signals to generate alternatively a unipolar electric field or a bipolar electric field by time division multiplexing for delivering the non-thermal energy to the tissue 41 to be treated.

In more detail, the single power source 4 of equipment 1000 of the invention can operate to deliver IRE energy according to a sequence of three types of voltage delivery that repeats.

In case of unipolar voltage only: voltage is applied from each electrode 3, 30, 31 to patient return electrode 5; this first step is followed by an off-period.

In case of unipolar and bipolar voltage combined: in a first step voltage is applied from each electrode 3, 30, 31 to patient return electrode 5; this first step is followed by a second step in which voltage is applied across two adjacent electrodes; both steps are followed by an off period.

According to an embodiment, by choosing the combined bipolar and unipolar, the ratio between bipolar and unipolar can be varied from 4 to 1 to all uni-polar.

By switching off the connection to the return electrode 5 in the ablation equipment 1000, and setting the phase shift of voltages Va and Vb to 180 degrees an all bi-polar mode can be produced.

Figure 2:
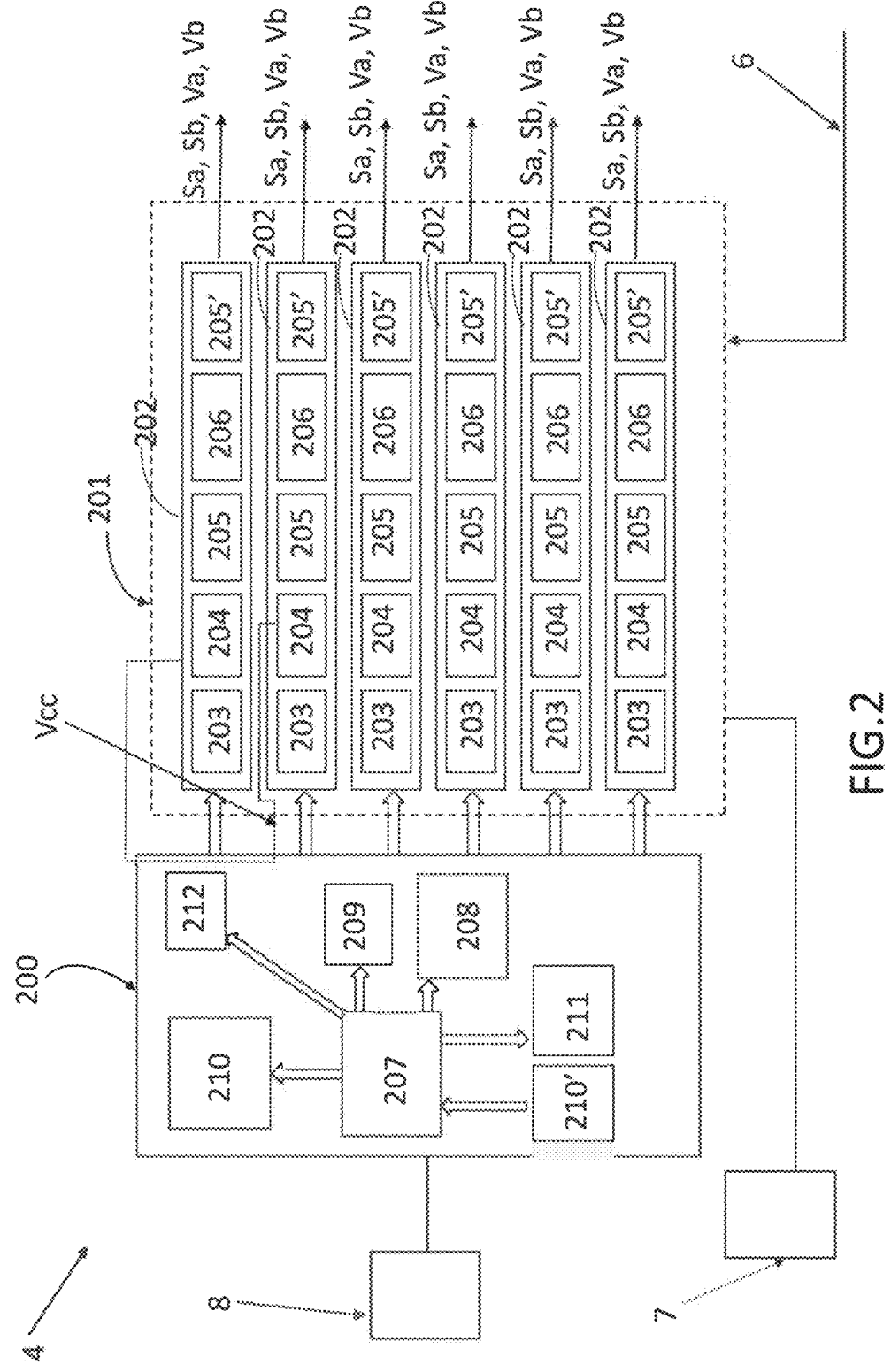
FIG. 2 shows block diagram of the single power source of the ablation equipment of FIG. 1 comprising a single control unit and a power unit.
Figure 3B:
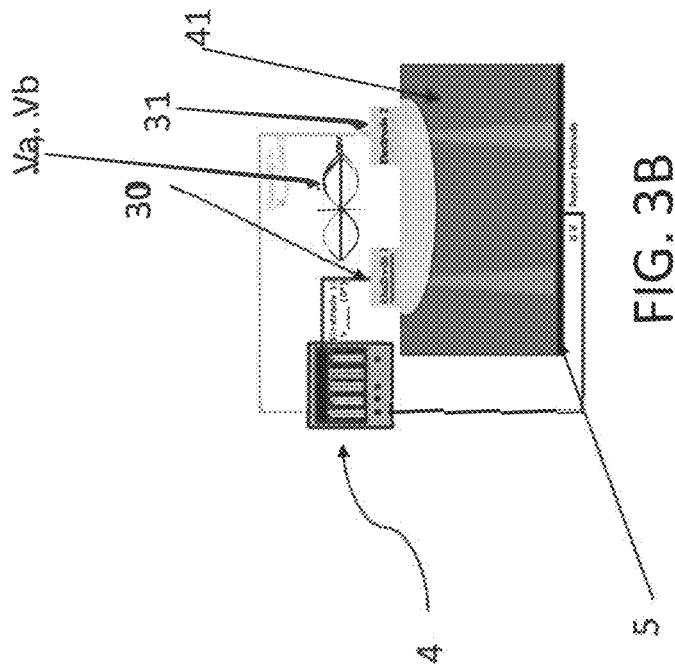
FIGS. 3A and 3B show schematically an ablation equipment for delivering non-thermal energy to treat target regions of tissue in organs according to the present invention, wherein the equipment comprises a first and a second electrodes positionable either on or near the tissue to be treated, and a single power source, this single power source being configured to supply both electrodes, respectively, with electrical sine-waves voltage signals "in phase" or with electrical sine-waves voltage signals "out of phase"
Figure 3A:
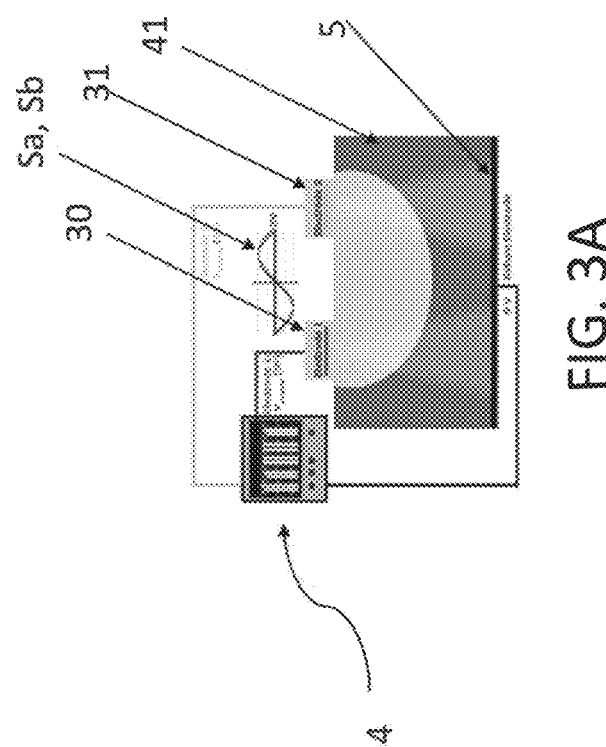
Figure 4:
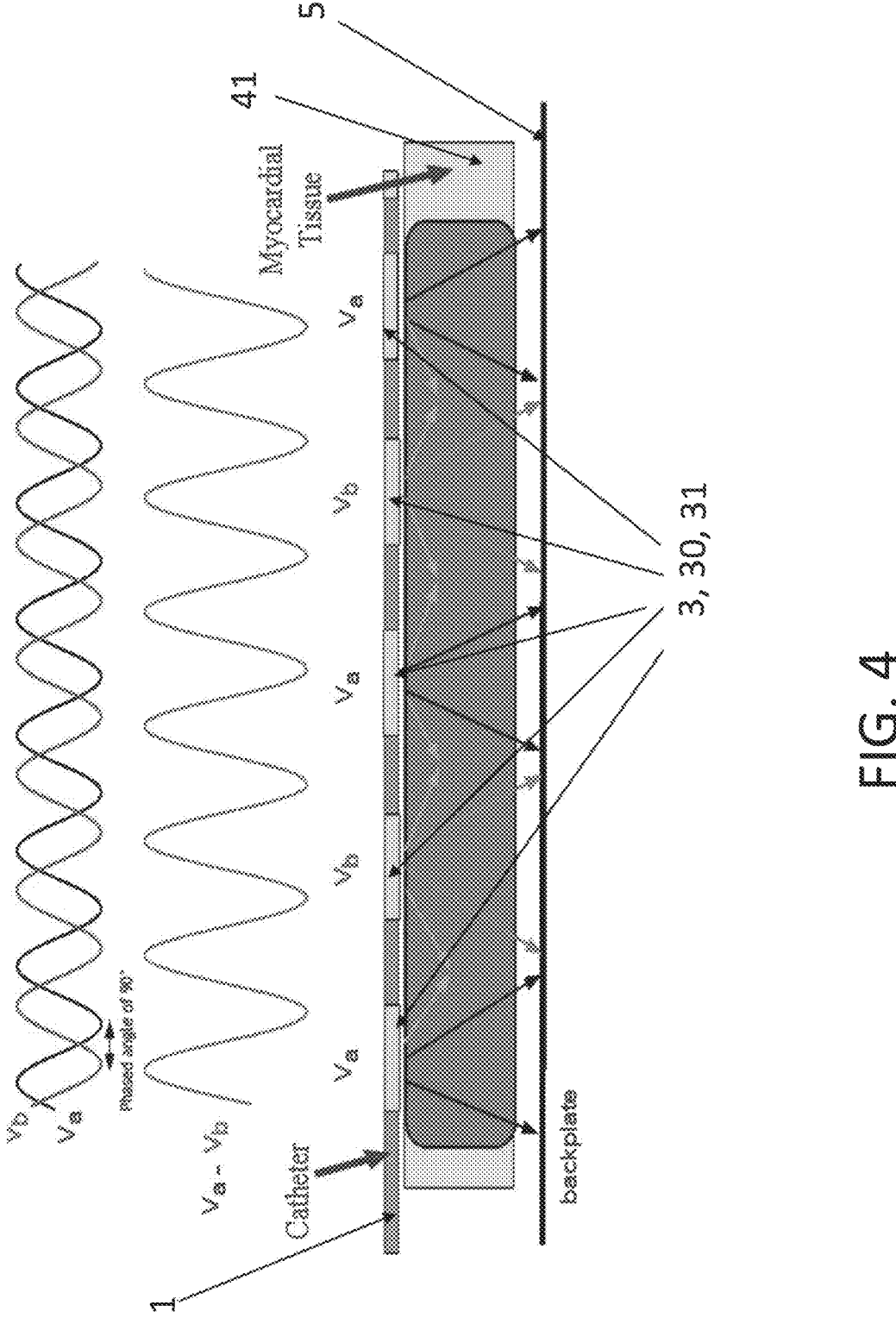
FIG. 4 shows schematically a plurality of electrodes electrically supplied by the single power source of equipment of FIG. 1, wherein said electrodes are operatively associated to a catheter and positionable either on or near a myocardial tissue to be treated, and are configured to deliver combined bi-polar and uni-polar voltages or alternating uni-polar and bi-polar voltage fields.

In accordance with an alternative embodiment, with reference to FIG. 2, the single power source 4 comprises a single control unit 200 and a power unit 201 for generating said sinusoidal electric voltage signals Sa, Sb, Va, Vb. The power unit 201 is electrically connected to all electrodes of said plurality of electrodes 3, 30, 31.

Figures 5A, 5B:
FIGS. 5A and 5B show, as a function of time, examples of electrical sine-waves voltage signals "in phase" or electrical sine-waves voltage signals "out of phase"
Figures 6A, 6B:
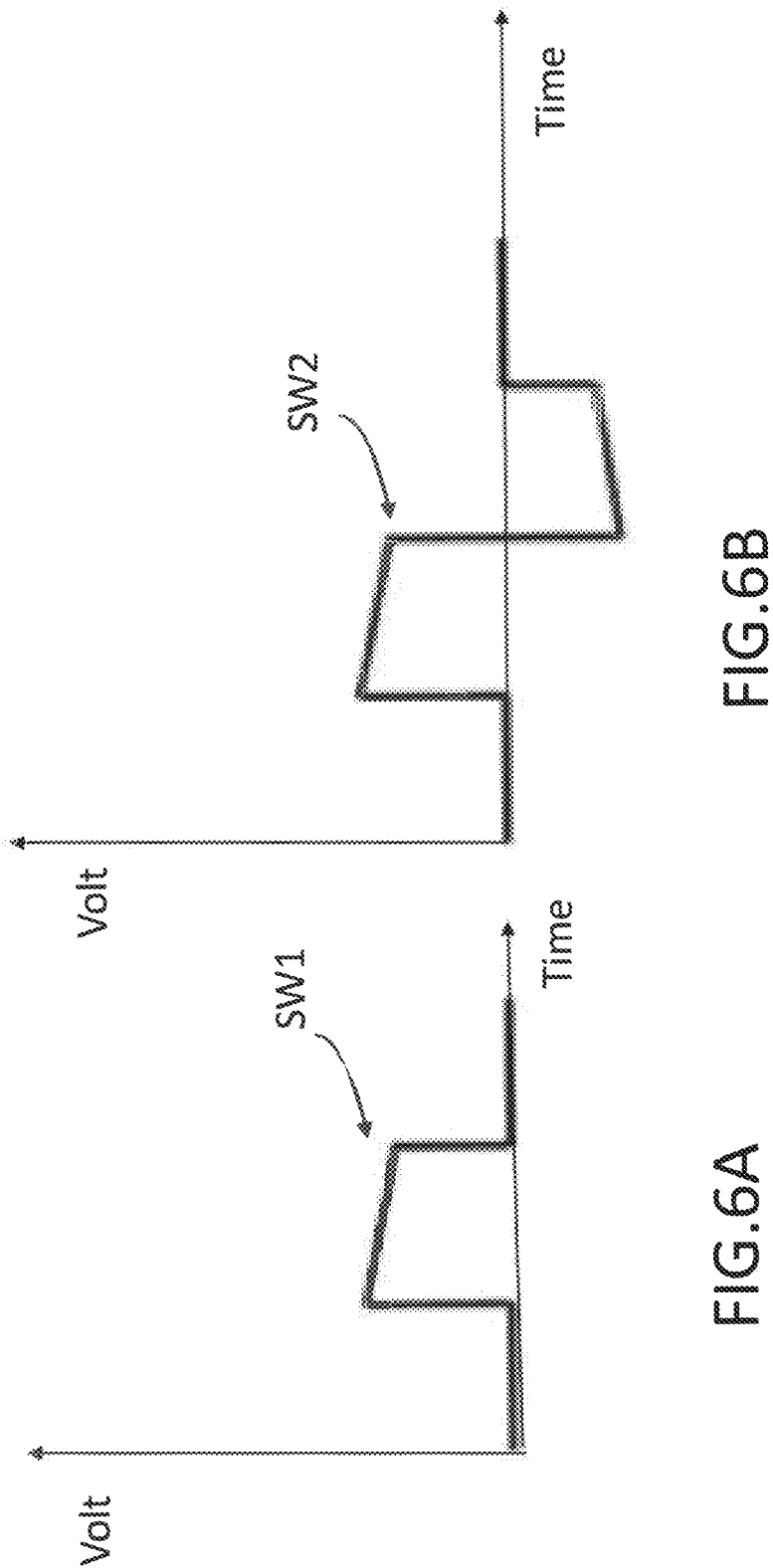
FIGS. 6A and 6B show, as a function of time, examples of square-wave PEF signals, respectively, monophasic and biphasic, known in the art.
Figure 7:
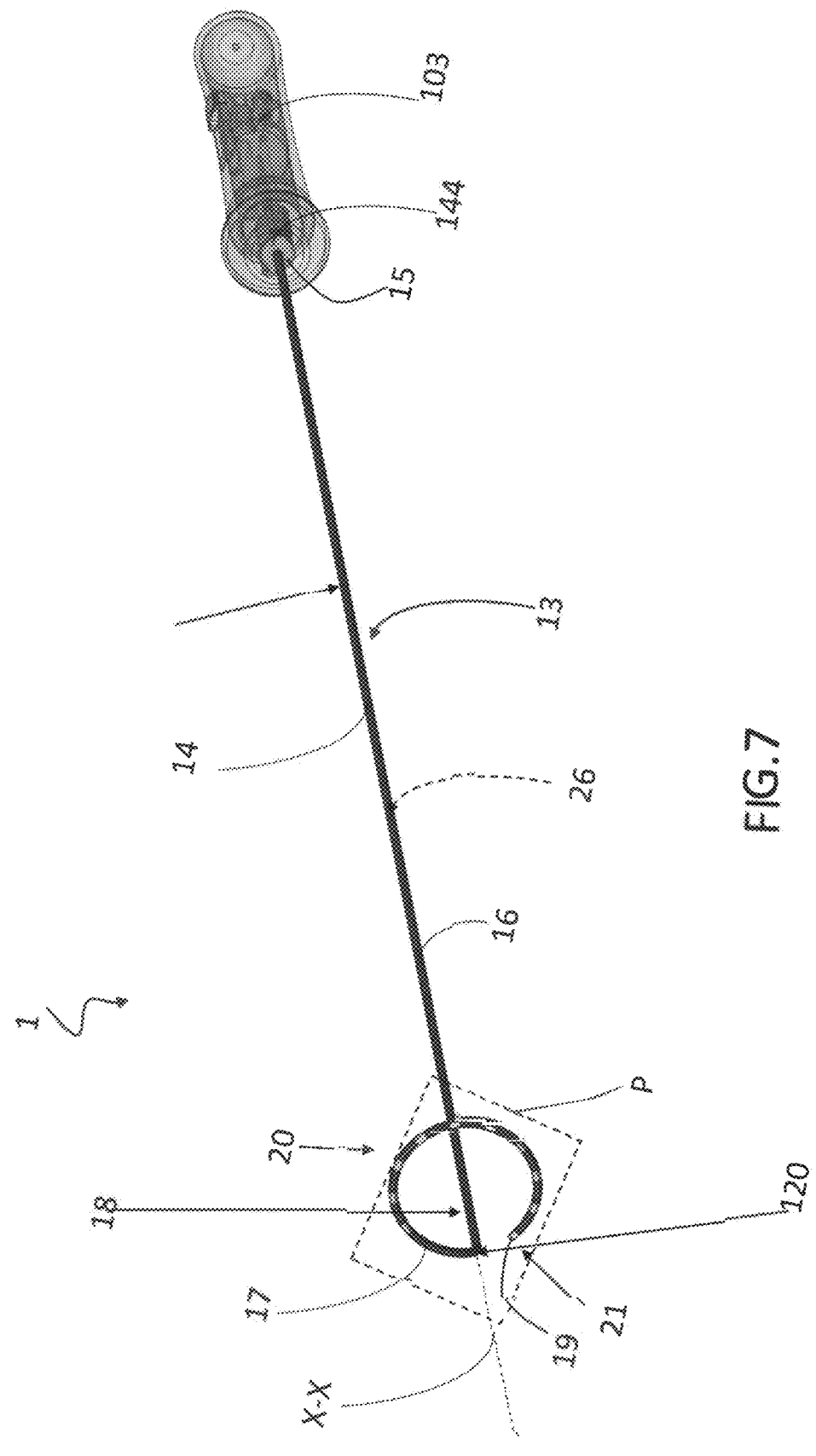
FIG. 7 is a perspective view of an ablation catheter that can be used in the ablation equipment of the invention, having an elongated shaft, and a shape setting mandrel disposed within the ablation catheter.
Figure 8:
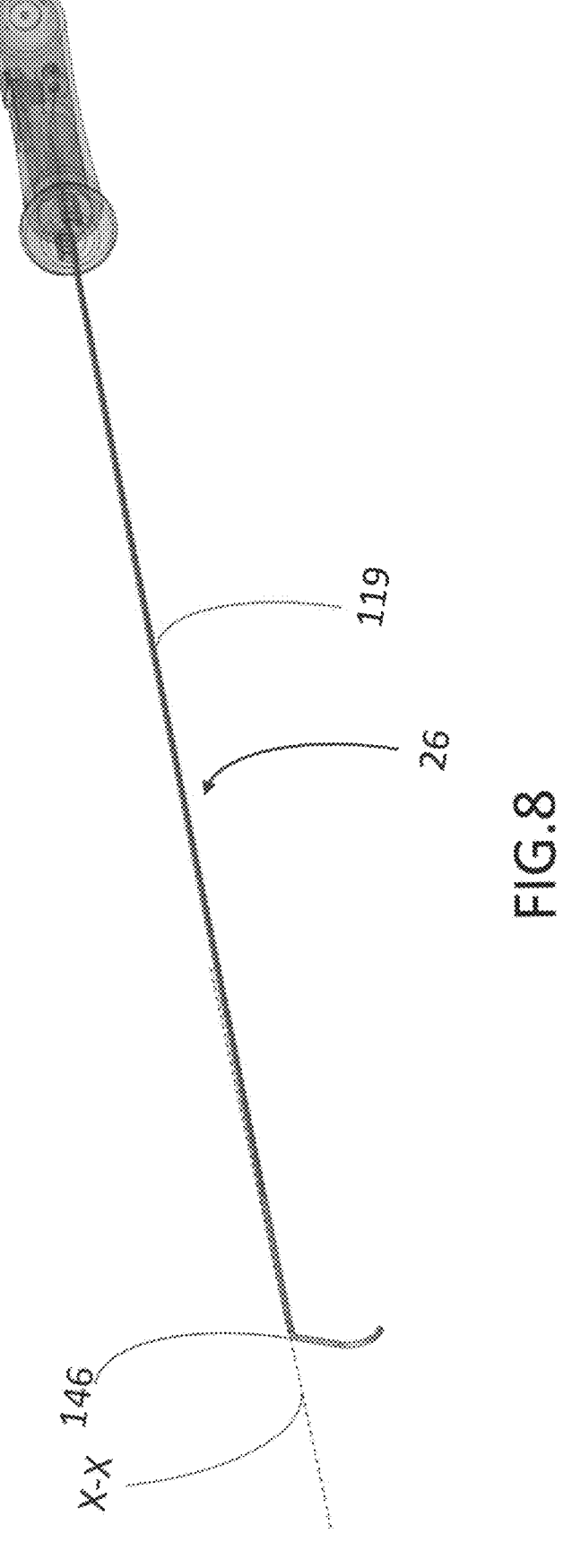
FIG. 8 shows the ablation catheter of FIG. 1, wherein the elongated shaft and the steering device are omitted, to show the shape setting mandrel partially inserted into the handle, wherein the shape setting mandrel has a bend preformed configuration.
Figure 10:
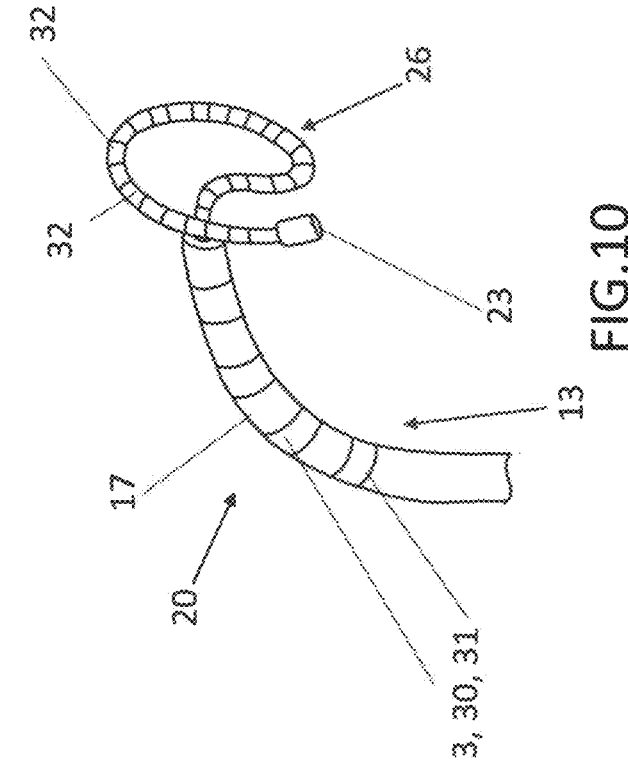
FIG. 10 is a perspective view of a distal portion of an ablation catheter that can be used in the ablation equipment of the invention, having an elongated shaft, and a shape setting mandrel having a circular preformed configuration disposed with its distal portion beyond a distal end of the elongated shaft, and wherein a distal portion of the elongated shaft is deflected in a deflection direction, wherein the shape setting mandrel comprises a plurality of mandrel electrodes disposed along its length, and the elongated shaft comprises a plurality of shaft electrodes.
Figure 9:
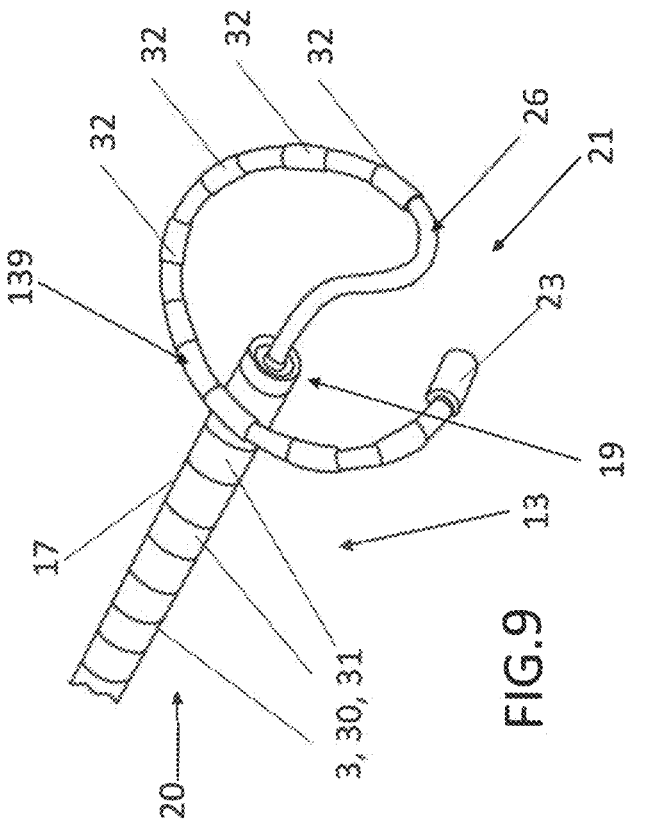
FIG. 9 is a perspective view of an ablation catheter that can be used in the ablation equipment of the invention, having an elongated shaft, and a shape setting mandrel having a circular preformed configuration disposed with its distal portion beyond a distal end of the elongated shaft.
Figures 11A, 11B, 11C:
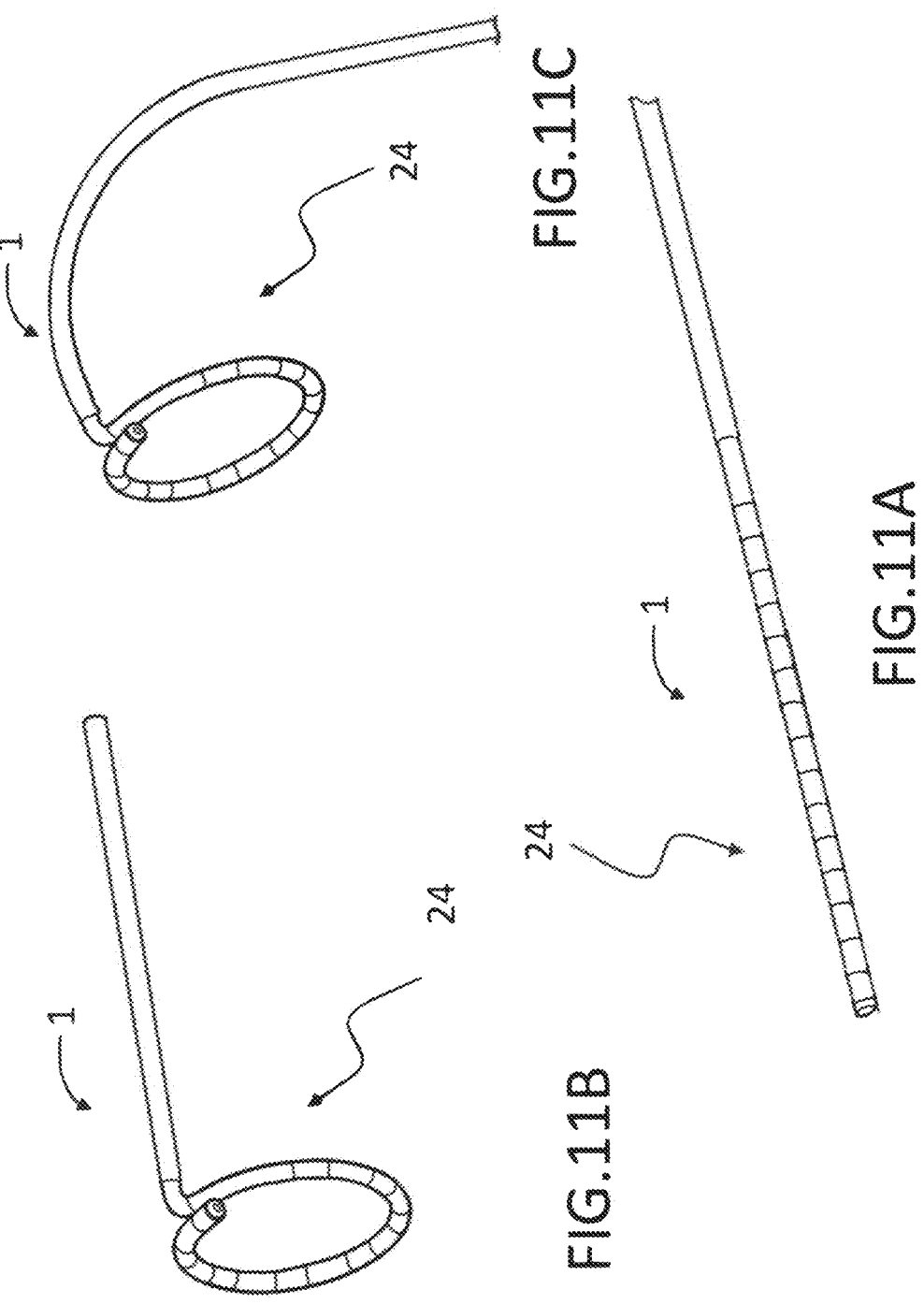
FIGS. 11A-11C show a shape setting mandrel respectively in a loaded straight configuration, in a preformed circular configuration, and in a preformed circular and bent configuration.
Figures 13A, 13B:
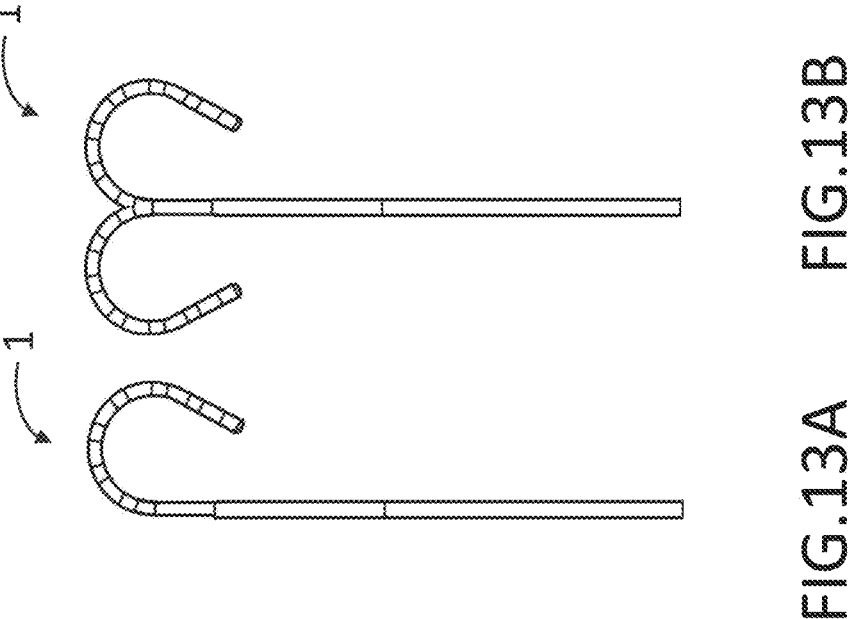
FIGS. 12A-12B and 13A-13B show a plurality of shape setting mandrels having different preformed configurations.
Figures 12A, 12B:
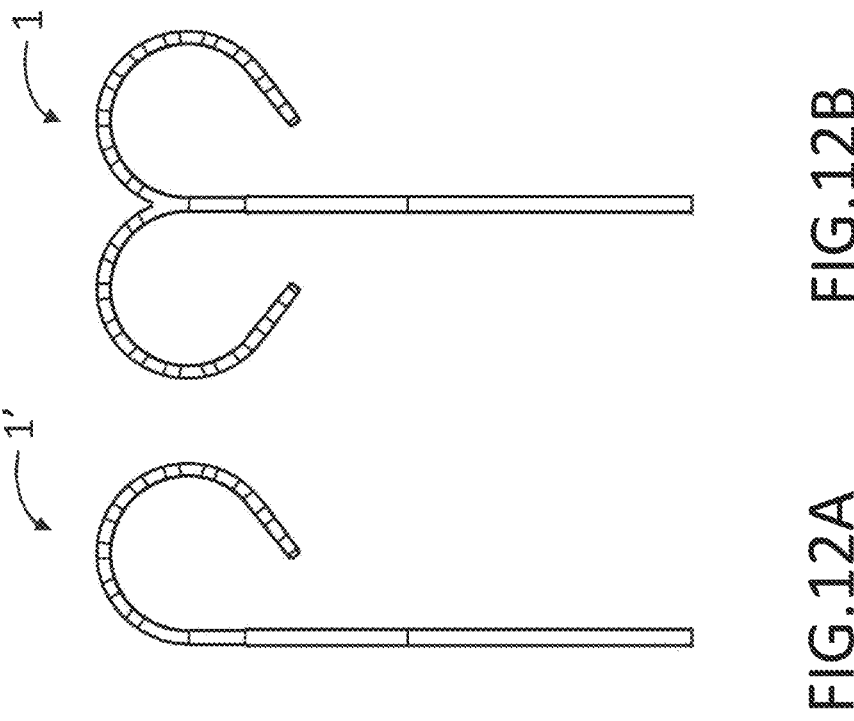
Figures 14A, 14B, 15:
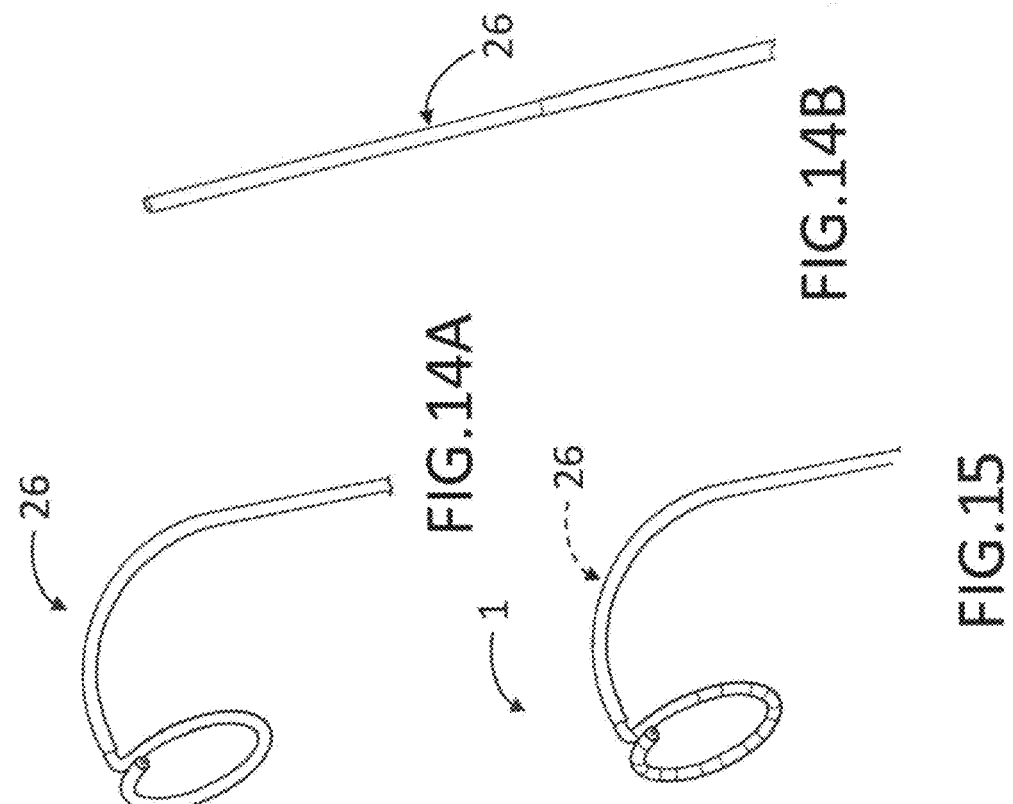
FIGS. 14A, 14B, and 15 show a shape setting mandrel respectively in a preformed circular and bent configuration and in a loaded straight configuration, and the shape setting mandrel in the preformed circular and bent configuration disposed within an ablation catheter.
Figure 17:
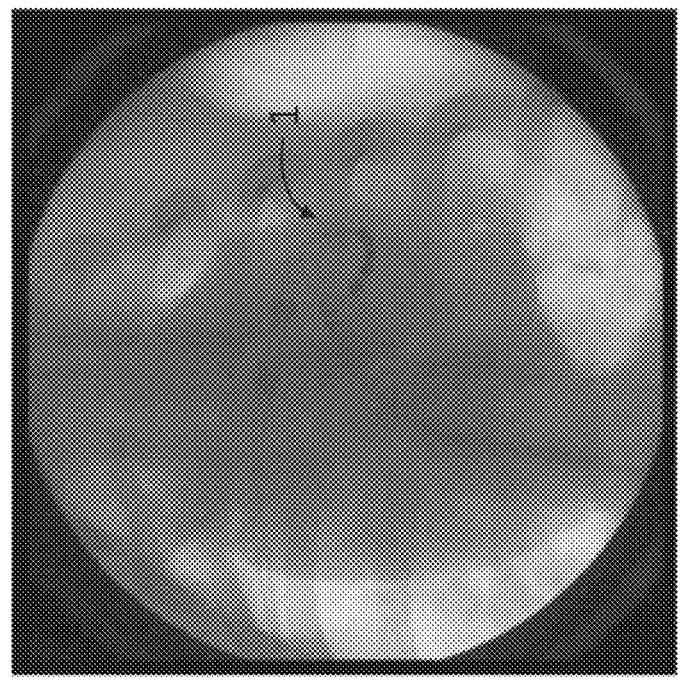
FIG. 17 shows a radiography of an ablation catheter according to the present invention, wherein a catheter distal portion is shape set as a pre-formed configuration of a shape setting catheter fully inserted into the catheter distal portion.
Figure 16:
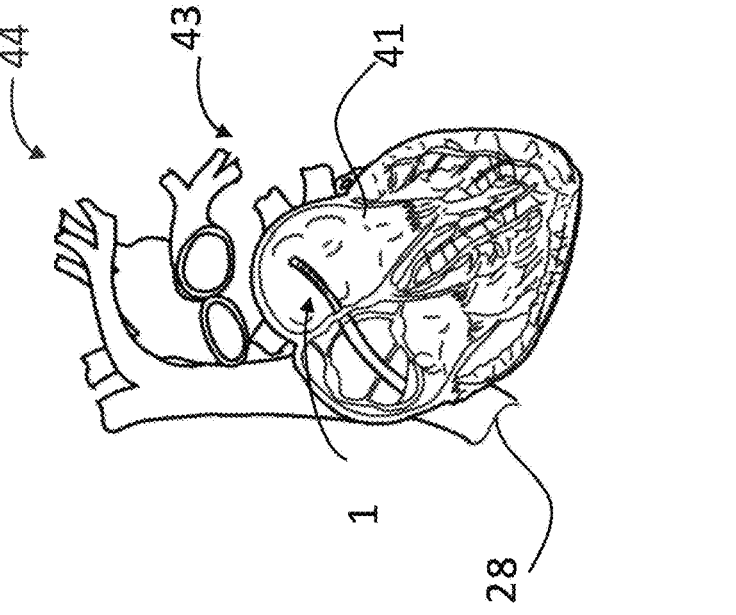
FIG. 16 shows an ablation catheter according to the present invention disposed within a heart, wherein a shape setting mandrel is fully inserted in a distal portion of the ablation catheter shaft.
Figures 18, 19, 20:
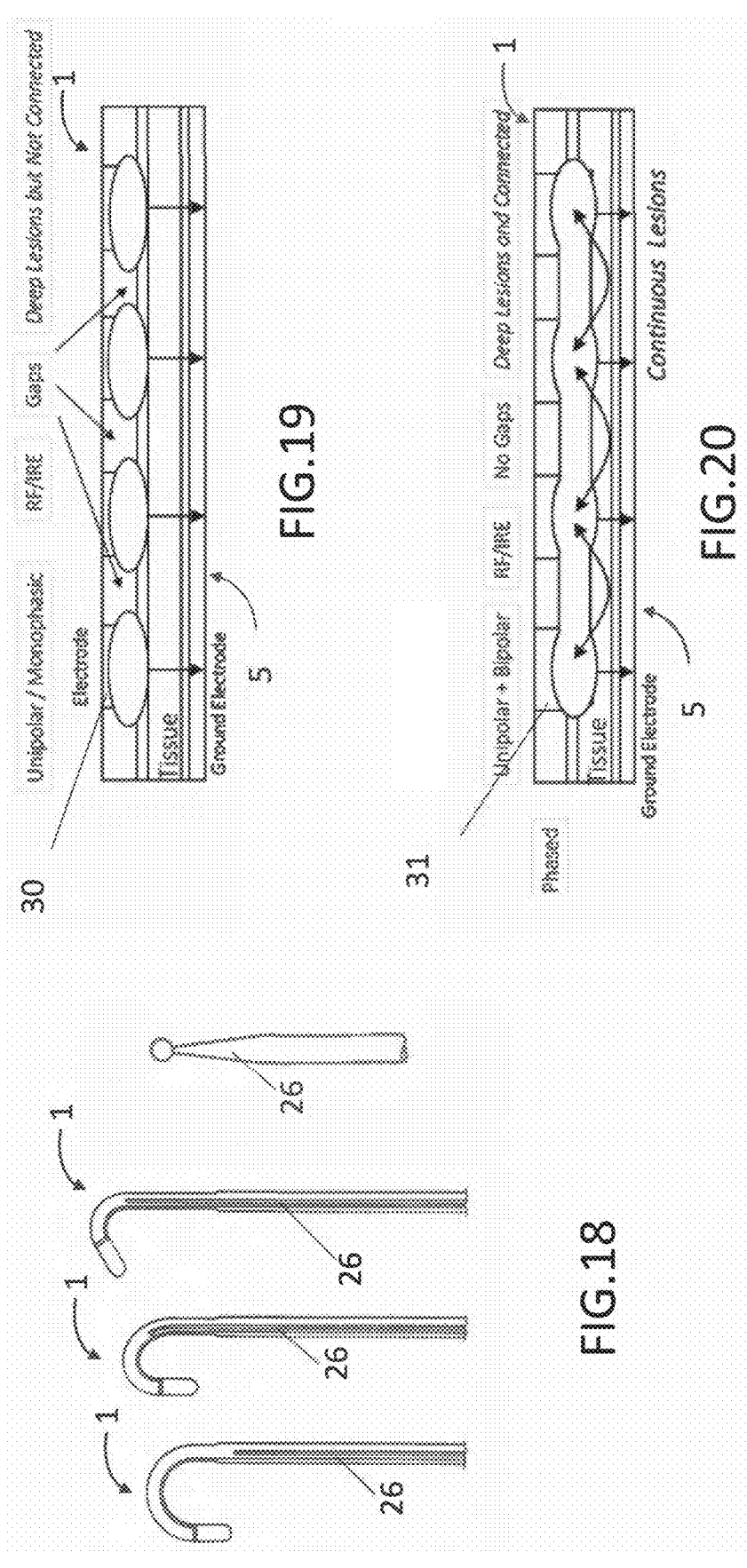
FIG. 18 shows a section side view of different ablation catheters and different shape setting mandrels disposed within the ablation catheter, and a shape setting mandrel having a rounded distal end.
FIG. 19 shows an example of operation of the ablation equipment of the invention to generate monopolar electric field from each electrode with a ground electrode.
FIG. 20 shows an example of operation of the ablation equipment of the invention to generate both a monopolar electric field from each electrode with a ground electrode and a bipolar electric field between two adjacent electrodes.
Figure 21:
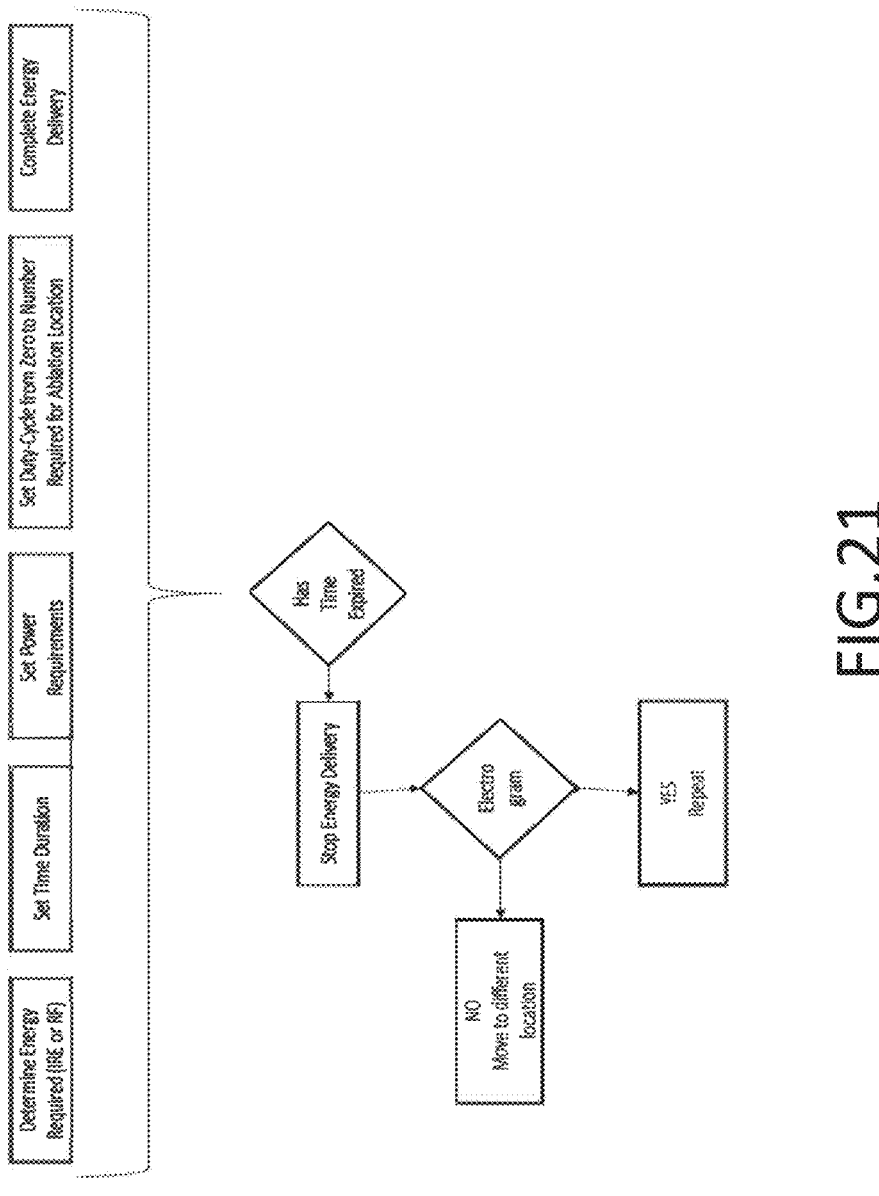
FIG. 21 shows a flux diagram of a method for ablation with an ablation assembly of the present invention.
Figure 22:
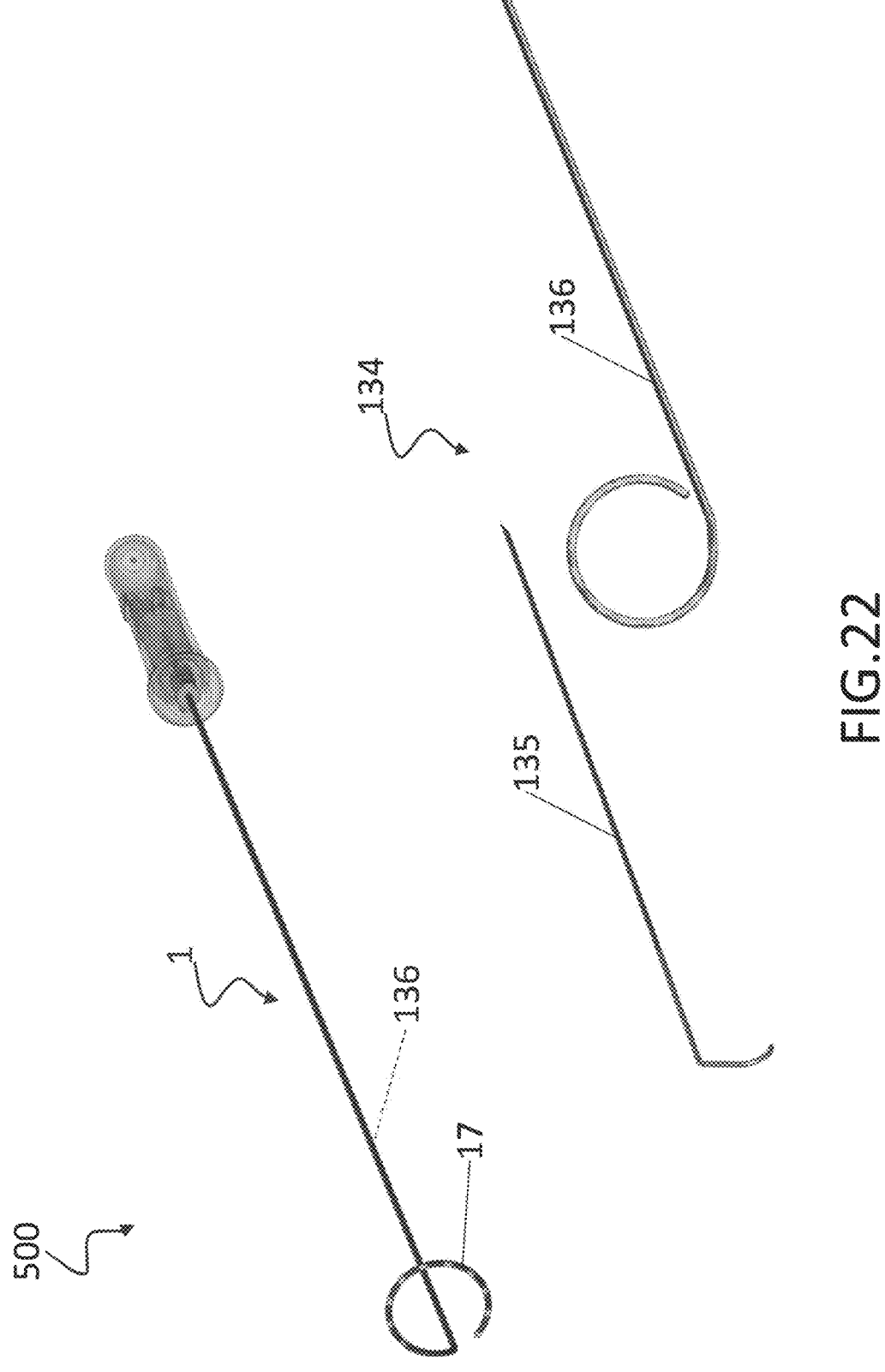
FIG. 22 shows an ablation kit comprising at least an ablation catheter and a set of shape setting mandrels.
Figure 23:
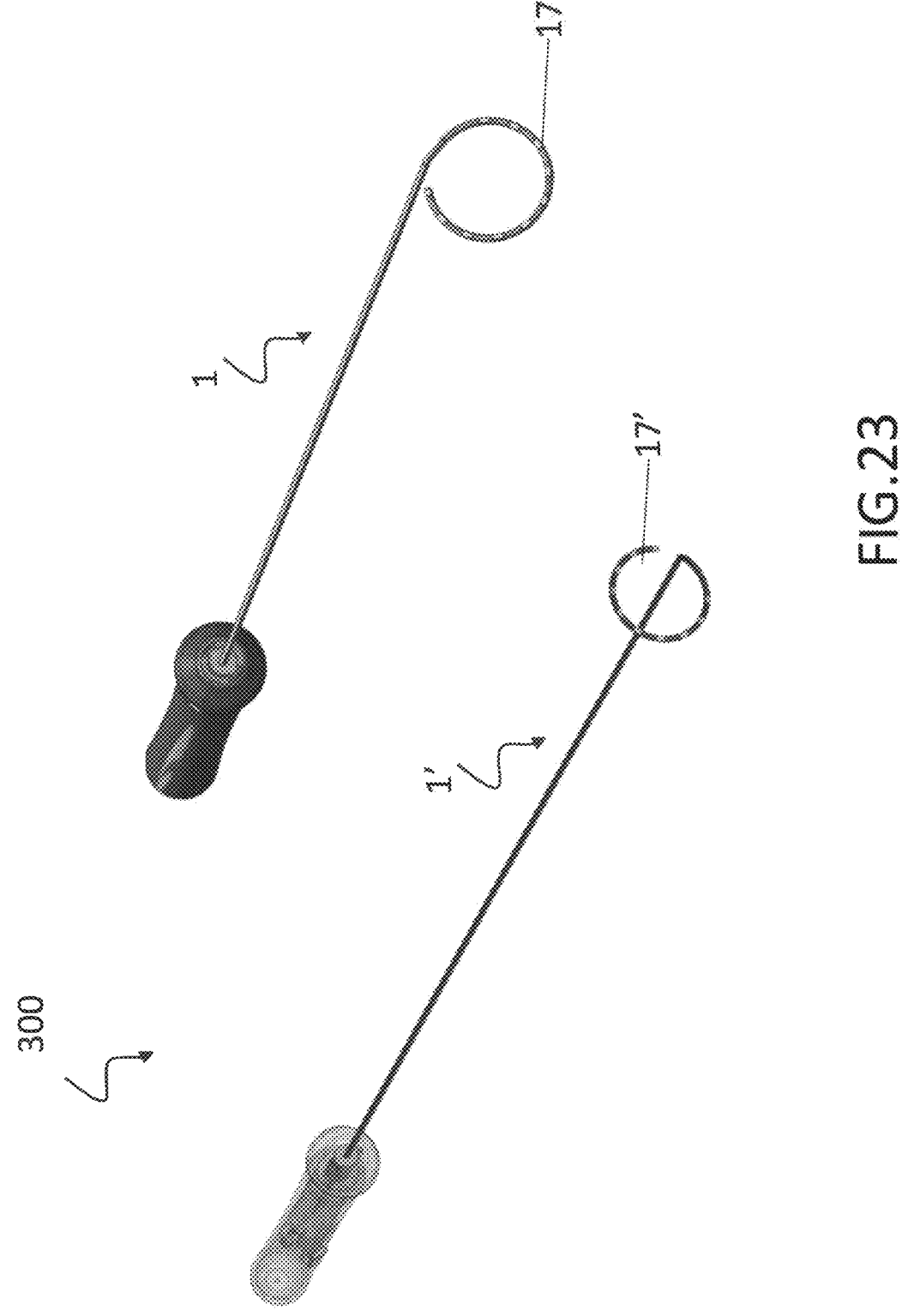
FIG. 23 shows an ablation catheter kit comprising a first ablation catheter and a second ablation catheter having different deflection configurations.

In accordance with an alternative embodiment, the first Sa and second Sb sinusoidal electric voltage signals "in phase" are supplied to the at least first 30 and second 31 electrodes during a first voltage delivery time interval T1. FIG. 5A shows the first voltage delivery time interval T1 including a single period of signals Sa, Sb, but the first voltage delivery time interval T1 could comprise several periods of these signals.

The single control unit 200 is configured to drive the power unit 201 to modify the duration of said first voltage delivery time interval T1 to change the level of the unipolar non-thermal energy delivered to the tissue 41 to be treated.

In accordance with an alternative embodiment, the further first Va and further second Vb sinusoidal electric voltage signals "out of phase" are supplied to the at least first 30 and second 31 electrodes during a second voltage delivery time interval T2. FIG. 5B shows the second voltage delivery time interval T2 including a single period of signals Va, Vb, but the second voltage delivery time interval T2 could comprise several periods of these signals.

The single control unit 200 is configured to drive the power unit 201 to modify the duration of said second voltage delivery time interval T2 to change the level of the unipolar and/or unipolar and bipolar non-thermal energy delivered to the tissue 41 to be treated.

In accordance with an alternative embodiment, the power unit 201 comprises one or more power modules 202 equal to each other, each power module being controlled by the single control unit 200 for generating said sinusoidal electric voltage signals Sa, Sb, Va, Vb starting from a constant supply voltage signal Vcc provided by the single control unit 200.

In accordance with an embodiment, each power module 202 comprises:
- a drive circuit block 203 controlled by the single control unit 200 for generating said sinusoidal electric voltage signals Sa, Sb, Va, Vb starting from the constant supply voltage signal Vcc provided by the single control unit 200;
- a selecting block 204 selectively controlled by said drive circuit block 203 to change continuously the electric energy level associated to said signals Sa, Sb, Va, Vb;
- a filtering and electrical isolation block 205, 205', 206.

In accordance with an embodiment, the single control unit 200 comprises:
- a Microprocessor 207 configured to control a variable High Voltage Power Supply block 208 and a Programmable Logic Controller block 209;
- said variable High Voltage Power Supply block 208 is configured to provide the supply voltage signal Vcc to the power module 202 for generating the sinusoidal electric voltage signals Sa, Sb, Va, Vb;
- said Programmable Logic Controller block 209 is configured to generate drive signals to control a drive circuit block 203 of the power module 202.

The single control unit 200 further comprises:
- a Video interface and Push Button block 210, 210' controlled by the Microprocessor 207 to set parameters of the ablation equipment 1000 and display the selected parameters;
- a Watch Dog block 211 for controlling proper functioning of the Microprocessor 207;
- an Audio interface block 212 for providing audio information representative of correctness of the ablation process and/or errors occurred. In some embodiments, control unit 200 includes a processor (e.g. microprocessor 207) and a memory coupled to the processor. The memory can store instructions for the processor to perform one or more algorithms. In some embodiments, an algorithm of the present invention is configured to titrate or otherwise determine an amount of calcium or other agent to be delivered as part of a non-thermal ablation using electroporation energy. For example, the algorithm can be based on data collected from the same or similar patients having received a non-thermal ablation using an agent.

In accordance with an embodiment, the single power source 4 is powered by a rechargeable battery or is connected to a standard wall outlet of an AC electrical power grid capable of producing 110 volts or 240 volts.

In accordance with an embodiment, the single power source 4 comprises an Electrocardiogram, ECG, interface 7 configured to connect the power unit 201 to an ECG diagnostic device.

In accordance with an embodiment, the single power source 4 comprises a wireless communication interface 8 connected to the single control unit 200 to allow the control unit to be remotely controlled.

In accordance with an embodiment, the power unit 201 comprises one or more power modules 202 equal to each other. Particularly, with reference to the example of FIG. 2, the power unit 201 comprises six power modules 202.

At least one of said electrodes 3, 30, 31 is a monopolar electrode, and said monopolar electrode of said plurality of electrodes is electrically connected to only one power module 202 of said power unit 201.

At least two of said electrodes 3, 30, 31 are electrically connected to form bipolar electrodes, and said bipolar electrodes of said plurality of electrodes are electrically connected separately to a respective power module 202 that is selectable among the power modules of the power unit 201.

In accordance with an embodiment, the single control unit 200 is configured to drive the power unit 201 to modify the frequencies of said sinusoidal electric voltage signals Sa, Sb, Va, Vb to change the level of the unipolar and/or unipolar and bipolar non-thermal energy delivered to the tissue 41.

In accordance with an embodiment, the power unit 201 is driven by the single control unit 200 to change the electric energy level associated to the voltage signals Sa, Sb, Va, Vb to be supplied to the electrodes 3, 30, 31 to switch from the non-thermal energy to a thermal energy, particularly Radio Frequency, RF, energy and vice-versa.

In accordance with an embodiment, the single control unit 200 drives the power unit 201 for generating said sinusoidal electric voltage signals Sa, Sb, Va, Vb by using a Proportional-Integral-Derivative, PID, control loop which receives information from at least one electrode 3, 30, 31 on the ablation catheter 1 and from the ECG diagnostic device through the ECG interface 7 such as to provide closed loop energy delivery based on measured and analyzed bio-signals.

In accordance with an embodiment, the at least an electrode 3, 30, 31 on the ablation catheter 1 comprises a mass filter/digital converter to measure said bio-signals to be provided to the single control unit 200.

In accordance with an embodiment, the single control unit 200 drives the power unit 201 for generating said sinusoidal electric voltage signals Sa, Sb, Va, Vb according to a first set of ablation parameters when a first type of ablation catheter 1 is connected to the single power source 4 and according to a second set of ablation parameters when a second type of ablation catheter 1' is connected to the single power source 4.

In accordance with an embodiment, with reference to FIGS. 7-23, the ablation catheter 1 comprises an elongated shaft 13 having a longitudinal main direction X-X. The elongated shaft 13 comprises at least a shaft distal portion 17, said shaft distal portion 17 comprising a shaft distal portion distal end 19.

The ablation catheter 1 comprises an inner lumen arranged within the elongated shaft 13.

The ablation catheter 1 comprises a shaft ablation assembly 20 fixedly disposed at said shaft distal portion 17, the shaft ablation assembly 20 being configured to deliver non-thermal energy, particularly IRE energy, for treating said tissue 41.

The ablation equipment 1000 comprises at least a shape setting mandrel 26 disposed within the ablation catheter 1. The shape setting mandrel 26 is insertable within the inner lumen and removable from the inner lumen. The shape setting mandrel 26 is free to move in respect of the inner lumen avoiding any constraint with said shaft distal portion 17 during the shape setting mandrel insertion.

The shape setting mandrel 26 comprises at least a pre-shaped configuration and the shape setting mandrel 26 is reversibly deformable between at least a straight loaded configuration and said pre-shaped configuration.

When the shape setting mandrel 26 is fully inserted in the shaft distal portion 17, the shape setting mandrel 26 is configured to shape set said shaft distal portion 17 with said pre-shaped configuration.

In accordance with an embodiment, the shaft distal portion 17 is elastically deformable, and/or when the shape setting mandrel 26 is fully inserted in the shaft distal portion 17, said shaft distal portion 17 is configured to conform to said pre-shaped configuration.

In accordance with an embodiment, the shape setting mandrel 26 is fully inserted in the shaft distal portion 17, said shape setting mandrel 26 deforms said shaft distal portion 17 at least in a shaft distal portion plane P.

In accordance with an embodiment, the ablation catheter 1 comprises a catheter bend portion 120 proximal to the shaft ablation assembly 20, wherein said catheter bend portion 120 is configured to realize an elbow that steers said shaft distal portion plane P with respect to said longitudinal main direction X-X.

In accordance with an embodiment, when the shape setting mandrel 26 is fully inserted in the shaft distal portion 17, the shaft distal portion 17 takes a circular configuration.

In accordance with an alternative embodiment, the shape setting mandrel 26 comprises a mandrel elastic body 119 capable to deform into at least said straight loaded configuration and to return to said pre-shaped configuration, and/or the shape setting mandrel 26 is made of at least a shape memory alloy; and/or the ablation equipment 1000 comprises a mandrel heating element coupled to said shape setting mandrel 26, wherein said heating element is configured to apply heat to said shape setting mandrel 26 so that the shape setting mandrel 26 changes shape configuration from said loaded straight configuration to said pre-shaped configuration.

In accordance with an embodiment, the shaft distal portion 17 is deflectable in one or more directions, in one or more deflections shapes and geometries 24.

In accordance with an embodiment, the shape setting mandrel 26 in the pre-shaped configuration is configured to maintain the deflections of the shaft distal portion 17 in a single plane, and/or the deflection directions are symmetric deflection geometries or asymmetric deflection geometries 24.

In accordance with an alternative embodiment, the ablation catheter 1 comprises an elongated shaft 13 with a proximal portion 14 including a shaft proximal end 15 and a distal end 16, and a distal portion 17 with a proximal end 18 and a distal end 19. In accordance with an alternative embodiment, said ablation catheter 1 comprises a steering device 144 attached to said shaft proximal end 15.

In accordance with an alternative embodiment, said ablation catheter 1 comprises a handle 103, wherein said steering device 144 is connected to said handle 103.

The elongated shaft 13 further comprises a distal ablation assembly 21 configured to deliver energy, such as RF and/or Irreversible Electroporation energy, to the tissue 41.

In accordance with an alternative embodiment, said shape setting mandrel 26 in said pre-shaped configuration comprises a mandrel bend portion 146, and when said shape setting mandrel 26 is fully inserted in said shaft distal portion 17, said mandrel bend portion 146 is disposed in correspondence of said catheter bend portion 120 performing said catheter bend portion 120.

In accordance with an alternative embodiment, said distal ablation assembly 21 is fixedly disposed at a mandrel distal portion 139.

In accordance with an alternative embodiment, said distal ablation assembly 21 comprises a plurality of mandrel electrodes 32, wherein said mandrel electrodes 32 are axially spaced along said mandrel distal portion 139.

In accordance with an alternative embodiment, said mandrel electrodes 32 comprise at least a tip ablation element 23.

The present invention furthermore refers to a method for controlling at least a plurality of electrodes 3, 30, 31 in an ablation equipment 1000 for delivering non-thermal energy, particularly IRE energy, to treat target regions of tissue 41 in organs 44, wherein the ablation equipment 1000 comprises an ablation catheter 1 and a single power source 4.

The method comprises the following steps:

generating by the single power source 4 electric voltage signals Sa, Sb, Va, Vb to energize each electrode of the at least a plurality of electrodes 3, 30, 31, wherein each of said electric voltage signals Sa, Sb, Va, Vb is a sinusoidal wave; and supplying, by the single power source 4, at least a first 30 and a second 31 electrodes that are adjacent to each other on said ablation catheter 1, with sinusoidal electric voltage signals in phase with each other or out of phase with each other to generate a unipolar electric field and/or a bipolar electric field to be delivered to the tissue 41 to be treated.

In accordance with an alternative embodiment, the method further comprises the steps of:

supplying, by the single power source 4, the at least a first 30 and a second 31 electrodes with a first Sa and a second Sb sinusoidal electric voltage signals, respectively, the first Sa sinusoidal electric voltage signal having a phase difference 1 with the second Sb sinusoidal electric voltage signal equal to 0 degrees;

generating a unipolar electric field from each of said first 30 and second 31 electrodes to a patient return electrode 5 for delivering unipolar non-thermal energy only to the tissue 41 to be treated.

In accordance with an alternative embodiment, the method further comprises the steps of:

supplying, by the single power source 4, the at least a first 30 and a second 31 electrodes with a further first Va and a further second Vb sinusoidal electric voltage signals, respectively;

varying a phase difference 1 of the further first Va sinusoidal electric voltage signal with the further second Vb sinusoidal electric voltage signal from 0 degrees to 180 degrees to generate both a unipolar electric field from each of said first 30 and second 31 electrodes to a patient return electrode 5 and to generate a bipolar electric field between said first 30 and second 31 electrodes for delivering simultaneously unipolar and bipolar non-thermal energy to the tissue 41 to be treated.

In accordance with an alternative embodiment, the method further comprises the steps of setting the phase difference 1 between said further first Va and further second Vb sinusoidal electric voltage signals to 180 degrees to generate a bipolar electric field between said first 30 and second 31 electrodes for delivering bipolar non-thermal energy only to the tissue 41 to be treated.

In accordance with an alternative embodiment, the method further comprises the step of setting the phase difference 1 between said further first Va and further second Vb sinusoidal electric voltage signals to 90 degrees to generate a bipolar electric field between said first 30 and second 31 electrodes which is double the unipolar electric field generated from each of said first 30 and second 31 electrodes to the patient return electrode 5.

In accordance with an alternative embodiment, the method further comprises the step of supplying, by the single power source 4, the at least a first 30 and a second 31 electrodes with sinusoidal electric voltage signals to generate alternatively a unipolar electric field or a bipolar electric field by time division multiplexing for delivering the non-thermal energy to the tissue 41 to be treated.

In accordance with an alternative embodiment, the method further comprises the steps of:
supplying, by the single power source 4, the first Sa and second Sb sinusoidal electric voltage signals "in phase" to the at least first 30 and second 31 electrodes during a first voltage delivery time interval T1;
modifying the duration of said first voltage delivery time interval T1 to change the level of the unipolar non-thermal energy delivered to the tissue 41 to be treated.

In accordance with an alternative embodiment, the method further comprises the steps of:
supplying, by the single power source 4, said further first Va and further second Vb sinusoidal electric voltage signals "out of phase" to the at least first 30 and second 31 electrodes during a second voltage delivery time interval T2;
modifying the duration of said second voltage delivery time interval T2 to change the level of the unipolar and/or unipolar and bipolar non-thermal energy delivered to the tissue 41 to be treated.

In accordance with an alternative embodiment, the method further comprises the steps of:
providing the single power source 4 which comprises a single control unit 200 and a power unit 201 for generating said sinusoidal electric voltage signals Sa, Sb, Va, Vb;
said power unit 201 is electrically connected to all electrodes of said plurality of electrodes 3, 30, 31;
said power unit 201 comprising one or more power modules 202 equal to each other;
controlling, by the single control unit 200, each power module for generating said sinusoidal electric voltage signals Sa, Sb, Va, Vb starting from a constant supply voltage signal Vcc provided by the single control unit 200.

In accordance with an alternative embodiment, the method further comprises the step of modifying, by the single control unit 200, the frequencies of said sinusoidal electric voltage signals Sa, Sb, Va, Vb to change the level of the unipolar and/or unipolar and bipolar non-thermal energy delivered to the tissue 41.

In accordance with an alternative embodiment, the method further comprises the step of switching, by the single control unit 200, from the non-thermal energy, particularly IRreversible Electroporation, IRE, energy, to a thermal energy, particularly Radio Frequency, RF, and vice versa to change the electric energy level associated to the voltage signals Sa, Sb, Va, Vb to be supplied to the electrodes 3, 30, 31.

The present invention furthermore refers to an ablation catheter kit 300 comprising at least a first ablation equipment having a first ablation catheter 1 and a second ablation equipment having a second ablation catheter 1'.

The shaft distal portion 17 of the first ablation catheter 1 is deflectable in at least two symmetric geometries. The shaft distal portion 17' of the second ablation catheter 1' is deflectable in at least two asymmetric geometries.

The present invention furthermore refers to an ablation catheter kit 500 comprising:
at least an ablation equipment 1000 having an ablation catheter 1 according to any one of the above described embodiments;
a set of shape setting mandrels 134.

The shape setting mandrels of said set 134 can have similar and/or different pre-shaped configurations. The shape setting mandrels of said set 134 are alternatively disposable and removable in said ablation catheter 1.

The present invention furthermore refers to use of the kit to treat both the left and right atria of a heart, wherein the ablation catheter 1 of the ablation equipment 1000 is used to ablate tissue in the right atrium using at least a first shape setting mandrel 135, and the same ablation catheter 1 is used to also ablate tissue in the left atrium using at least a second shape setting mandrel 136. In some embodiments, the first shape setting mandrel 135 comprises a different geometry than the second shape setting mandrel 136. In some embodiments, the first shape setting mandrel 135 and the second shape setting mandrel 136 comprise similar geometries.

Thanks to the solutions proposed, it is possible to provide a method for the treatment of proximal, persistent or long-standing persistent atrial fibrillation in a patient, comprising the following steps:
providing an ablation equipment 1000 according to any one of the above described embodiments;
placing the ablation catheter 1 in the coronary sinus of the patient, such as to deliver non-thermal energy for treating a tissue;
placing the ablation catheter 1 in the left or right atrium to deliver non-thermal energy for treating a tissue, wherein the tissue locations include fascicles around a pulmonary vein, and/or the left atrial roof, and/or the mitral isthmus.

Thanks to the solutions proposed, it is possible to provide a method for the treatment of atrial flutter in a patient comprising, the following steps:
providing an ablation equipment 1000 according to any one of the above described embodiments;
placing the ablation catheter 1 in one or more locations in the right atrium of the heart to achieve bi-directional block by delivering non-thermal energy for treating a tissue.

Thanks to the solutions proposed, it is possible to provide a method of ablating tissue in the right atrium of the heart, comprising the following steps:
providing an ablation equipment 1000 according to any one of the above described embodiments;
placing the ablation catheter 1 in one or more locations in the right (and/or left) atrium of the heart 43;
creating lesions between the superior vena cava and the inferior vena cava and/or the coronary sinus and the inferior vena cava and/or the superior vena cava and the coronary sinus by delivering non-thermal energy for treating a tissue.

Thanks to the solutions proposed, it is possible to provide a method for the treatment of sinus node tachycardia in a patient, comprising the following steps:
providing an ablation equipment 1000 according to any one of the above described embodiments;
placing the ablation catheter 1 in one or more locations in the right (and/or left) atrium of the heart 43;

ablating the sinus node by delivering non-thermal energy for treating a tissue.

Thanks to the solutions proposed, it is possible to provide a method for the treatment of ventricular tachycardia in a patient, comprising the following steps:

providing an ablation equipment 1000 according to any one of the above described embodiments;

placing the ablation catheter 1 in the left or right ventricles of the heart 43;

inducing ventricular tachycardia by delivering pacing energy, and ablating tissue to treat the patient by delivering non-thermal energy for treating a tissue.

Thanks to the solutions proposed, it is possible to provide a method to ablate atrial tissues, comprising the following steps, comprising the following steps:

providing an ablation equipment 1000 according to any one of the above described embodiments, wherein the shaft distal portion 17 comprises a first deflection geometry when the shape setting mandrel 26 is fully inserted in the elongated shaft 13, and the shaft distal portion 17 comprises a second deflection geometry when the shape setting mandrel 26 is removed from the shaft distal portion 17, wherein the first deflection geometry is larger than the second deflection geometry;

placing the ablation catheter 1 exposed to an atrial tissue, with the shaft distal portion 17 in the second deflection geometry with said shape setting mandrel 26 outside said distal portion 17;

ablating one or more of the following tissue locations: left atrial septum; tissue adjacent the left atrial septum; and tissue adjacent the left atrial posterior wall by delivering both non-thermal energy for treating a tissue and thermal energy for ablating a tissue;

placing the ablation catheter 1 with the shaft distal portion 17 in the first deflection geometry by fully inserting the shape setting mandrel 26 within the elongated shaft 13, ablating at least the circumference of tissue around the pulmonary veins by delivering both non-thermal energy for treating a tissue and thermal energy for ablating a tissue.

The ablation equipment 1000 and related methods of the present invention provides relevant advantages.

For example, the single power source 4 configured to generate the sinusoidal electric voltage signals Sa, Sb, Va, Vb rely on transformers. Therefore, a high level of electrical isolation is ensured for the patient.

Furthermore, the ablation equipment 1000 of the invention ensures a high degree of flexibility for energy delivery by modifying the phase difference of the signals, their frequencies and the delivery times T1, T2. Therefore, lengths and depths of lesions caused by the IRE procedure can be tailored.

In addition, the Applicant has verified that the cost of components to design and manufacture the ablation equipment 1000 for delivering sinusoidal-waves is significantly less than the cost for manufacturing generators of a square-wave known in the art.

In addition, alternating current (AC) signals with simple spectral content, like the sine wave signals, represent a much better option, with different frequency components of the electric field having overlapping effects on the cell membrane during energy delivery.

LIST OF REFERENCE NUMERALS

1000 ablation equipment
1 ablation catheter OR energy delivery system OR energy delivery device OR probe OR multi-electrode and multi-functional ablation catheter
3, 30, 31 electrode
4 single power source OR energy source OR non-thermal energy source OR generator OR power delivery source OR IRE generator
5 patient return electrode OR ground electrode
6 return wire
7 ECG interface
8 wireless communication interface
9 wire
13 elongated shaft
14 elongated shaft proximal portion
15 elongated shaft proximal end
16 elongated shaft distal end
17 elongated shaft distal portion
18 elongated shaft distal portion proximal end
19 elongated shaft distal portion distal end
20 shaft ablation assembly
21 mandrel ablation assembly
23 tip ablation element
24 deflections shapes and geometries
26 shape setting mandrel OR shape setting center mandrel
27 flexible body
28 body vessels
Φ phase difference
32 mandrel electrode
41 tissue
43 heart
44 organ
103 handle
119 mandrel elastic body
120 catheter bend portion
134 set of shape fitting mandrel
135 first shape setting mandrel
136 second shape setting mandrel
139 mandrel distal portion
144 steering device
146 mandrel bend portion
500 Kit of ablation catheter and set of mandrels
300 kit of ablation catheters
IRE irreversible electroporation
RF radiofrequency
X-X elongated shaft longitudinal main direction
P shaft distal portion plane
200 single control unit OR means for selectively energizing the electrodes
201 power unit
202 power module OR outputs of the IRE generator
203 drive circuit block
204 selecting block
205, 205' filtering block
206 electrical isolation block
207 Microprocessor
208 variable High Voltage Power Supply block
209 Programmable Logic Controller block
210 Video interface and Push Button block
211 Watch Dog block
212 Audio interface block
S sinusoidal electric voltage signal
Sa first sinusoidal electric signal Sb second sinusoidal electric signal
Va further first sinusoidal electric signal
Vb further second sinusoidal electric signal
Vcc supply voltage signal

What is claimed is:

1. Ablation equipment for delivering non-thermal energy to treat target regions of tissue in organs of a subject, the ablation equipment comprising:

an ablation catheter comprising:

a catheter elongated shaft comprising an elongated shaft distal portion, wherein the catheter elongated shaft comprises a flexible body to navigate through body vessels;

a shaft ablation assembly disposed at the elongated shaft distal portion and a distal ablation assembly extending out from the elongated shaft distal portion, wherein the shaft ablation assembly comprises a first plurality of electrodes fixedly disposed at the elongated shaft distal portion and a second plurality of electrodes fixedly disposed along the distal ablation assembly; and a power source electrically connected to the first plurality of electrodes and the second plurality of electrodes, wherein the power source is configured to generate electric voltage signals to energize each of the first plurality of electrodes and the second plurality of electrodes for delivering non-thermal energy to the tissue to be treated;

wherein each of the electric voltage signals is a sinusoidal wave, and wherein the power source is configured to supply at least a first electrode and an adjacent second electrode of the first plurality of electrodes with sinusoidal electric voltage signals that are in phase with each other or out of phase with each other to generate a unipolar electric field and/or a bipolar electric field for delivering the non-thermal energy to the tissue to be treated;

wherein the power source comprises a control unit and a power unit for generating the sinusoidal electric voltage signals, wherein the power unit is electrically connected to each of the first plurality of electrodes and the second plurality of electrodes; and wherein the power unit comprises one or more power modules equal to each other, and each power module is controlled by the control unit for generating the sinusoidal electric voltage signals starting from a constant supply voltage signal provided by the control unit.

2. The ablation equipment according to claim 1, wherein the power source is configured to supply the first electrode with a first sinusoidal electric voltage signal and to supply the second electrode with a second sinusoidal electric voltage signal, wherein the first and second sinusoidal electric voltage signals comprise a phase difference equal to 0 degrees, and wherein the first and second sinusoidal electric voltage signals are configured to generate a unipolar electric field from each of the first and second electrodes to a patient return electrode for delivering unipolar non-thermal energy only to the tissue to be treated.

3. The ablation equipment according to claim 1, wherein the power source is configured to supply the first electrode with a first sinusoidal electric voltage signal and to supply the second electrode with a second sinusoidal electric voltage signal, wherein the first and second sinusoidal electric voltage signals comprise a phase difference that can be varied from 0 degrees to 180 degrees, and wherein the first and second sinusoidal electric voltage signals are configured to generate both a unipolar electric field from each of the first and second electrodes to a patient return electrode and to generate a bipolar electric field between the first and second electrodes for delivering simultaneously unipolar and bipolar non-thermal energy to the tissue to be treated.

4. The ablation equipment according to claim 3, wherein the phase difference between the first and second sinusoidal electric voltage signals is 180 degrees, and wherein the first and second sinusoidal electric voltage signals are configured to generate the bipolar electric field between the first and second electrodes for delivering the bipolar non-thermal energy only to the tissue to be treated.

5. The ablation equipment according to claim 3, wherein the phase difference between the first and second sinusoidal electric voltage signals is 90 degrees, and wherein the first and second sinusoidal electric voltage signals are configured to generate the bipolar electric field between the first and second electrodes which is double the unipolar electric field generated from each of the first and second electrodes to the patient return electrode.

6. The ablation equipment according to claim 1, wherein a peak-to-peak mean amplitude of each sinusoidal electric voltage signal is between 500 V and 5000 V.

7. The ablation equipment according to claim 6, wherein the peak-to-peak mean amplitude is 3500 V.

8. The ablation equipment according to claim 1, wherein the power source is configured to supply the first and second electrodes with sinusoidal electric voltage signals that are configured to generate alternatively a unipolar electric field or a bipolar electric field by time division multiplexing for delivering the non-thermal energy to the tissue to be treated.

9. The ablation equipment according to claim 1, wherein the first and second sinusoidal electric voltage signals comprise signals that are in phase with each other, wherein the first and second sinusoidal electric voltage signals are supplied to the first and second electrodes during a first voltage delivery time interval, and wherein the control unit is configured to drive the power unit to modify a duration of the first voltage delivery time interval to change a level of the unipolar non-thermal energy delivered to the tissue to be treated.

10. The ablation equipment according to claim 1, wherein the first and second sinusoidal electric voltage signals comprise signals that are out of phase with each other, wherein the first and second sinusoidal electric voltage signals are supplied to the first and second electrodes during a second voltage delivery time interval, and wherein the control unit is configured to drive the power unit to modify a duration of the second voltage delivery time interval to change a level of the unipolar and/or unipolar and bipolar non-thermal energy delivered to the tissue to be treated.

11. The ablation equipment according to claim 1, wherein each power module comprises:

a drive circuit block controlled by the control unit and configured to generate the sinusoidal electric voltage signals starting from the constant supply voltage signal provided by the control unit;

a selecting block selectively controlled by the drive circuit block and configured to continuously change an electric energy level associated to the sinusoidal electric voltage signals; and a filtering and electrical isolation block.

12. The ablation equipment according to claim 1, wherein the control unit comprises a microprocessor configured to control a variable high voltage power supply block and a programmable logic controller block, wherein the variable high voltage power supply block is configured to provide a supply voltage signal to a power module for generating the sinusoidal electric voltage signals, wherein the programmable logic controller block is configured to generate drive signals to control a drive circuit block of the power module, and wherein the control unit further comprises:

a video interface and push button block controlled by the microprocessor to set parameters of the equipment and display the parameters;

a watch dog block for controlling proper functioning of the microprocessor; and an audio interface block for providing audio information representative of correctness of an ablation process and/or errors occurred.

13. The ablation equipment according to claim 1, wherein the power source is powered by a rechargeable battery or is connected to a standard wall outlet of an AC electrical power grid capable of producing 110 volts or 240 volts.

14. The ablation equipment according to claim 1, wherein the power source comprises an ECG interface configured to connect a power unit to an ECG diagnostic device.

15. The ablation equipment according to claim 1, wherein the power source comprises a wireless communication interface connected to a control unit, and wherein the wireless communication interface is configured to allow the control unit to be remotely controlled.

16. The ablation equipment according to claim 1, wherein the non-thermal energy is irreversible electroporation energy.

17. The ablation equipment according to claim 1, wherein the power unit comprises two or more power modules that are equal to each other, wherein at least one of the first plurality of electrodes or at least one of the second plurality of electrodes is a monopolar electrode that is electrically connected to a power module of the power unit, and wherein at least two of the first plurality of electrodes or at least two of the second plurality of electrodes are electrically connected to form bipolar electrodes that are electrically and separately connected to respective power modules that are selectable among the two or more power modules.

18. The ablation equipment according to claim 1, wherein the control unit is configured to drive the power unit to modify frequencies of the sinusoidal electric voltage signals to change a level of the unipolar and/or unipolar and bipolar non-thermal energy delivered to the tissue.

19. The ablation equipment according to claim 1, wherein the power unit is driven by the control unit to change an electric energy level associated with the sinusoidal electric voltage signals to be supplied to the first plurality of electrodes and the second plurality of electrodes to switch from the non-thermal energy to a thermal energy.

20. The ablation equipment according to claim 1, wherein the control unit drives the power unit for generating the sinusoidal electric voltage signals by using a PID control loop configured to receive information from at least one electrode of the first plurality of electrodes or at least one electrode of the second plurality of electrodes and from an ECG diagnostic device through an ECG interface, wherein the PID control loop provides closed loop energy delivery based on measured and analyzed bio-signals.

21. The ablation equipment according to claim 20, wherein the at least one electrode of the first plurality of electrodes or the at least one electrode of the second plurality of electrodes comprises a mass filter/digital converter to measure the bio-signals to be provided to the control unit.

22. The ablation equipment according to claim 1, wherein the control unit drives the power unit for generating the sinusoidal electric voltage signals according to a first set of ablation parameters when a first type of ablation catheter is connected to the power source and according to a second set of ablation parameters when a second type of ablation catheter is connected to the power source.

23. The ablation equipment according to claim 1, further comprising a composition comprising one or more calcium salts for use in a treatment of non-thermal ablation of the tissue of the target region, wherein the ablation equipment is configured to provide the treatment comprising:

a) administering an effective amount of the composition to the subject via a systemic route of administration; and b) delivering non-thermal ablative energy to the tissue of the target region.

24. The ablation equipment according to claim 23, wherein cell membrane permeability of the tissue of the target region is increased by administration of the composition, and wherein administration leads to a cell apoptotic process, with depletion of ATP and increased intracellular calcium concentration.

* * * * *